US011577025B2

(12) United States Patent
Dix et al.

(10) Patent No.: US 11,577,025 B2
(45) Date of Patent: Feb. 14, 2023

(54) DEVICES AND METHODS FOR OVERFILLING DRUG CONTAINERS

(71) Applicant: Regeneron Pharmaceuticals Inc., Tarrytown, NY (US)

(72) Inventors: Daniel B. Dix, Fort Myers, FL (US); Douglas Kamen, Poughquag, NY (US); Kenneth Graham, Pleasant Valley, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 99 days.

(21) Appl. No.: 16/626,677

(22) PCT Filed: Jun. 29, 2017

(86) PCT No.: PCT/US2017/040011
§ 371 (c)(1),
(2) Date: Dec. 26, 2019

(87) PCT Pub. No.: WO2019/005072
PCT Pub. Date: Jan. 3, 2019

(65) Prior Publication Data
US 2020/0155760 A1 May 21, 2020

(51) Int. Cl.
*A61M 5/178* (2006.01)
*B65B 3/00* (2006.01)

(52) U.S. Cl.
CPC ............ *A61M 5/1782* (2013.01); *B65B 3/003* (2013.01); *A61M 2202/30* (2013.01)

(58) Field of Classification Search
CPC ............ A61M 5/1782; A61M 2207/00; A61M 2202/30; B65B 3/003
(Continued)

(56) References Cited

U.S. PATENT DOCUMENTS 3,965,945 A 6/1976 Ross
4,357,971 A 11/1982 Friedman
(Continued)

FOREIGN PATENT DOCUMENTS

EP 1270412 A1 * 1/2003 ............... A61J 1/062
JP 2005118222 A * 5/2005 ........ A61M 5/31505
(Continued)

OTHER PUBLICATIONS

JP-2005118222-A English Translation of Specification (Year: 2022).*
(Continued)

*Primary Examiner* — Reinaldo Sanchez-Medina
*Assistant Examiner* — Stephanie A Shrieves
(74) *Attorney, Agent, or Firm* — Bookoff McAndrews, PLLC

(57) ABSTRACT

Disclosed herein are methods for overfilling primary packaging components, and drug products prepared according to those methods. The methods may include introducing a volume of a formulated drug substance into a primary packaging component having a nominal volume, where the volume of the formulated drug substance is greater than the nominal volume of the primary packaging component. In some cases, the primary packaging component may be a prefillable syringe.

22 Claims, 9 Drawing Sheets

(58) Field of Classification Search
USPC .......................................................... 141/2
See application file for complete search history.

(56) References Cited

U.S. PATENT DOCUMENTS

| | | | |
|---|---|---|---|
| 4,573,967 A | | 3/1986 | Hargrove et al. |
| 5,009,646 A | * | 4/1991 | Sudo ................. A61M 5/31513 604/230 |
| 5,538,506 A | | 7/1996 | Farris et al. |
| 5,685,846 A | * | 11/1997 | Michaels, Jr. .... A61M 5/31596 604/82 |
| 6,152,898 A | | 11/2000 | Olsen |
| 6,223,408 B1 | * | 5/2001 | Vetter ................... B65B 7/2821 29/234 |
| 6,382,035 B1 | | 5/2002 | Nichols |
| 6,877,530 B2 | | 4/2005 | Osborne et al. |
| 8,225,824 B2 | | 7/2012 | Eliuk et al. |
| 8,386,070 B2 | | 2/2013 | Eliuk et al. |
| 2001/0018937 A1 | | 9/2001 | Nemoto |
| 2003/0097098 A1 | | 5/2003 | Lavi et al. |
| 2004/0103951 A1 | * | 6/2004 | Osborne ................ B65B 3/003 141/27 |
| 2004/0182475 A1 | * | 9/2004 | Vetter ..................... B65B 3/003 141/311 R |
| 2005/0029307 A1 | * | 2/2005 | Py ........................ B65D 81/245 222/386 |
| 2006/0168916 A1 | * | 8/2006 | Griebel ................... B65B 3/003 53/489 |
| 2006/0287639 A1 | | 12/2006 | Sharp |
| 2007/0185439 A1 | * | 8/2007 | Sugita ................. A61M 5/3155 604/82 |
| 2009/0182284 A1 | * | 7/2009 | Morgan .............. A61M 5/3137 604/198 |
| 2011/0224610 A1 | * | 9/2011 | Lum ....................... A61M 5/36 141/2 |
| 2012/0164226 A1 | | 6/2012 | Leuthner et al. |
| 2015/0190578 A1 | * | 7/2015 | Okihara ................ B65B 7/2821 53/111 R |
| 2015/0314070 A1 | * | 11/2015 | Heintz ...................... F01B 1/01 222/1 |
| 2017/0341784 A1 | * | 11/2017 | Lumkemann ......... A61J 1/1468 |
| 2018/0105294 A1 | * | 4/2018 | Abboud .................. B65B 3/003 |
| 2018/0133375 A1 | * | 5/2018 | Shiozaki .............. A61L 31/048 |
| 2020/0023135 A1 | * | 1/2020 | Bogert .............. A61M 5/31515 |

FOREIGN PATENT DOCUMENTS

| | | |
|---|---|---|
| JP | 2005118222 A | 5/2005 |
| JP | 2007143957 A | 6/2007 |
| TW | 201521711 A | 6/2015 |
| WO | WO-9852632 A1 | 11/1998 |
| WO | WO-2004050038 A2 | 6/2004 |
| WO | 2017/047295 A1 | 3/2017 |

OTHER PUBLICATIONS

EP-1270412-A1 English Translation of Specification (Year: 2022).*
Official Communication in Japanese Patent Application No. 2019-571701 dated Jun. 1, 2021, with English translation (19 pages).
Allowable Excess Volume and Labeled Vial Fill Size in Injectable Drug and Biological Products, Guidance for Industry, U.S. Dept. of Health and Human Services, Pharmaceutical Quality/CMC, Jun. 2015, URL: (https://www.fda.gov/downloads/drugs/guidances/ucm389069.pdf), 8 pages.
Barlas S., "Controversy Looms Over Medicare's New Policy on 'Intentional Overfill' of Injectables," Pharmacy and Therapeutics, Dec. 2010, vol. 35 (12), pp. 656. URL: (https://www.ncbi.nlm.nih.gov/pmc/articles/PMC3008380/), 1 page.
Berteau C., et al., "Evaluation of the Impact of Viscosity, Injection Volume and Injection Flow Rate on Subcutaneous Injection Tolerance," Medical Devices: Evidence and Research, 2015, vol. 8, pp. 473-484, 12 pages.
Bruce A., "Amgen Suit Unveils Industry 'overfilling' Practices," vcstar.com, Article from Nov. 10, 2009, URL: (http://archive.vcstar.com/business/amgen-suit-unveils-industry-overfilling-practices-ep-370602974-350501951.html).
Cohen M.R. and Smetzer J.L., "Understanding and Managing Intravenous Container Overfill; Potential Dose Confusion," Hospital Pharmacy, ISMP Medication, Mar. 2014, vol. 49 (3), pp. 221-226. Article from Nov. 14, 2013, URL: (https://www.ismp.org/newsletters/acutecare/showarticle.aspx?id=63), Copyright 2014, Thomas Land Publishers, Inc.
Zimmermann, J., Comparing Lyophilization in Vials and Dual-Chamber Systems, PharmTech.com, Advancing Development and Manuafacturing, Feb. 15, 2012, Equipment and Processing Report, URL: (http://http://www.pharmtech.com/print/2089217page=full), Copyright 2020 UBM, 2 pages.
"Container Closure Systems for Packaging Human Drugs and Biologies," Guidance for Industry, U.S. Dept. of Health and Human Services, Chemistry, Manufacturing, and Controls Documentation, May 1999, 56 pages.
Eichberger C and Mastellone L., "Potent Isolated Syringe Filling Line for Clinical Trial Materials," Americal Pharmaceutical Review, Articles Jun. 24, 2012, URL: (http://www.americanpharmaceuticalreview.com/Featured-Articles/115287-Potent-Isolated-Syringe-Filling-Line-for-Clinical-Trial-Materials/).
Gaffney A.,"FDA Finalizes Guidance on Overfilling Injectable Vials," Regulatory Focus, News Article from Jun. 24, 2015, URL: (http://www.raps.org/Regulatory-Focus/News/2015/06/24/22756/FDA-Finalizes-Guidance-on-Overfilling-Injectable-Vials/).
Hitt E., "FDA Advises Checking Prefilled Syringes for Overfilling," Disclosures, [retrieved onMay 23, 2012]. Retrieved from the Internet: URL: (http://www.medscape.com/viewarticle/764431).
International Preliminary Report on Patentability and Written Report for the Application No. PCT/US2017/040011, dated Dec. 31, 2019, 14 pages.
International Search Report for the Application No. PCT/US2017/040011, dated Apr. 16, 2018, 8 pages.
Ochoa P.S. and Vega J.A.,"Concepts in Sterile Preparations and Aseptic Technique," (Book), Feb. 24, 2014, Edition: 1, Binding: Paperback, Publisher: Jones & Bartlett Learning, Published: Mar. 2014, , Calculations for Parenteral Compounding, pp. 102-103, 3 pages.
"Prefilled Syringes: Getting to the Point", Dec. 15, 2011, PharmaceuticalTechnology.com, URL: (http://www.pharmaceutical-technology.com/features/featureprefilled-syringes-getting-to-the-point/).
"Regeneron and Sanofi Announce First Approval of Kevzara™ (sarilumab) for the Treatment of Moderately to Severely Active Rheumatoid Arthritis in Adult Patients" by Health Canada, Regeneron, Feb. 1, 2017, 3 pages.
Regulatory Decision Summary, Kevzara, Health Canada, Date filed: Jan. 28, 2016, URL: (https://hpr-rps.hres.ca/reg-content/regulatory-decision-summary-detail.php?lang=en&linkID=RDS00205).
"Stoppering Techniques for Prefilled Syringes," Pharmaceutical Technology Editors Equipment and Processing Report, Dec. 17, 2008, URL: (http://www.pharmtech.com/stoppering-techniques-prefilled-syringes).
U.S. Pharmacopeia Pharmaceutical Dosage Forms, General Chapter 1151: Injections (Accessed Apr. 2, 2020) URL: (http://www.pharmacopeia.cn/v29240/usp29nf24s0_c1151_viewall.html).
U.S. Pharmacopeia Pharmaceutical Dosage Forms, General Chapter 1151: Injections, Pharmacopeial Forum, vol. 35(5), Sep.-Oct. 2009, undergoing revisions, URL: (http://www.usp.org/sites/default/files/usp_pdf/EN/USPNF/pharmaceuticalDosageForms.pdf), 14 pages.

* cited by examiner

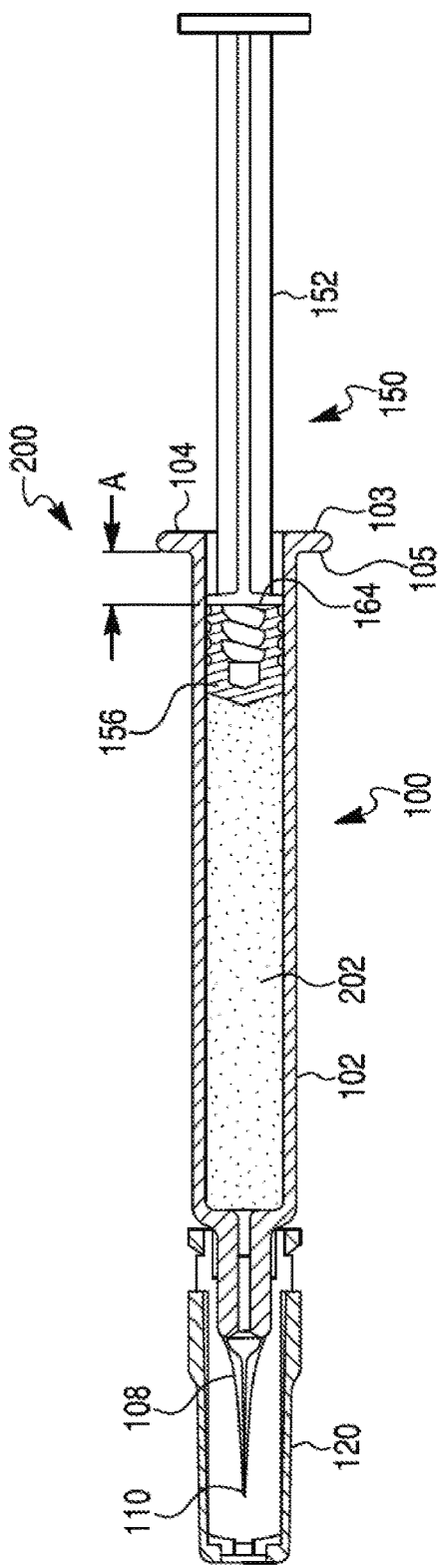
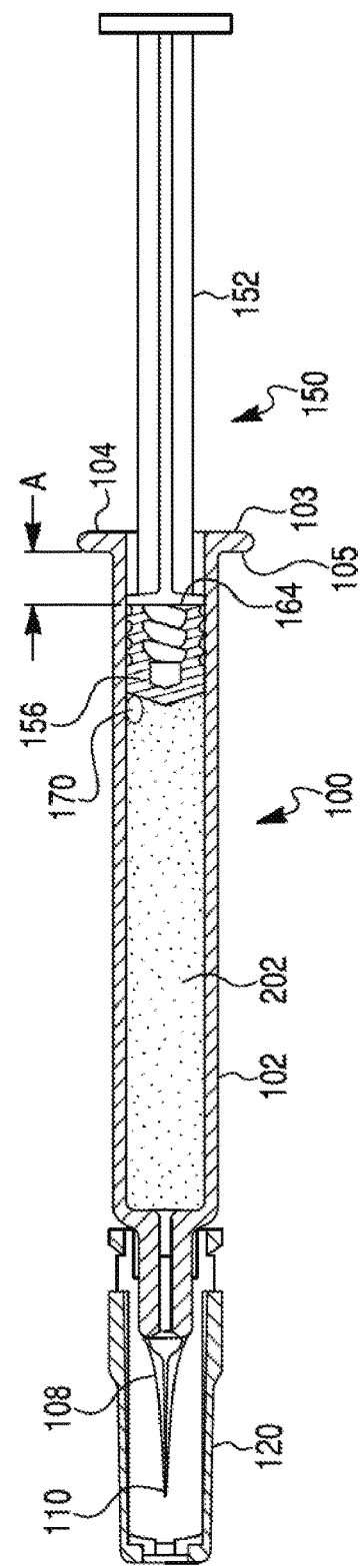

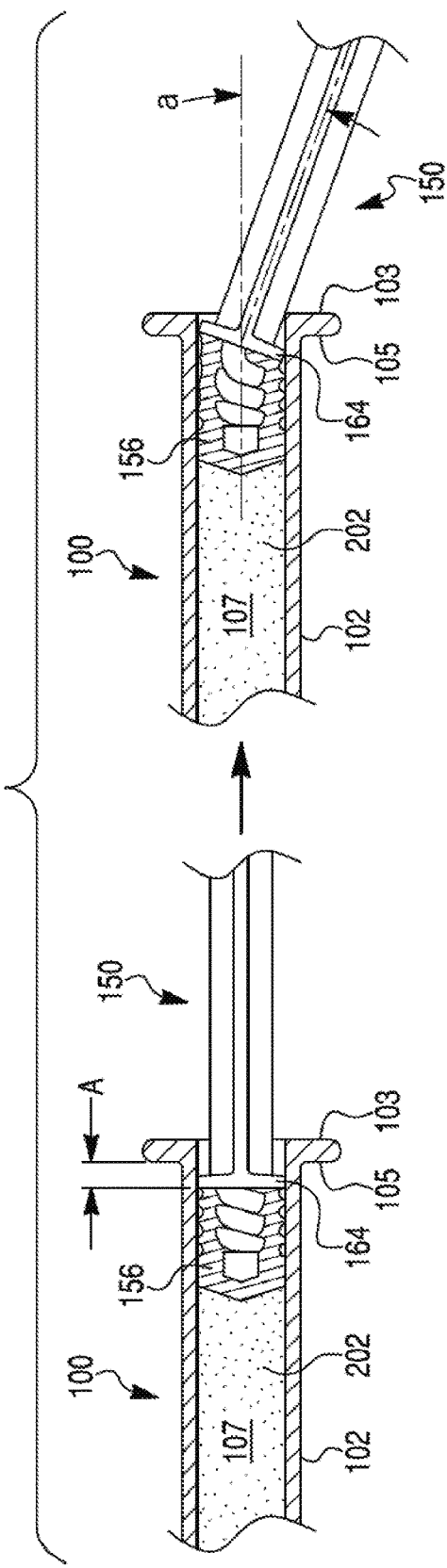
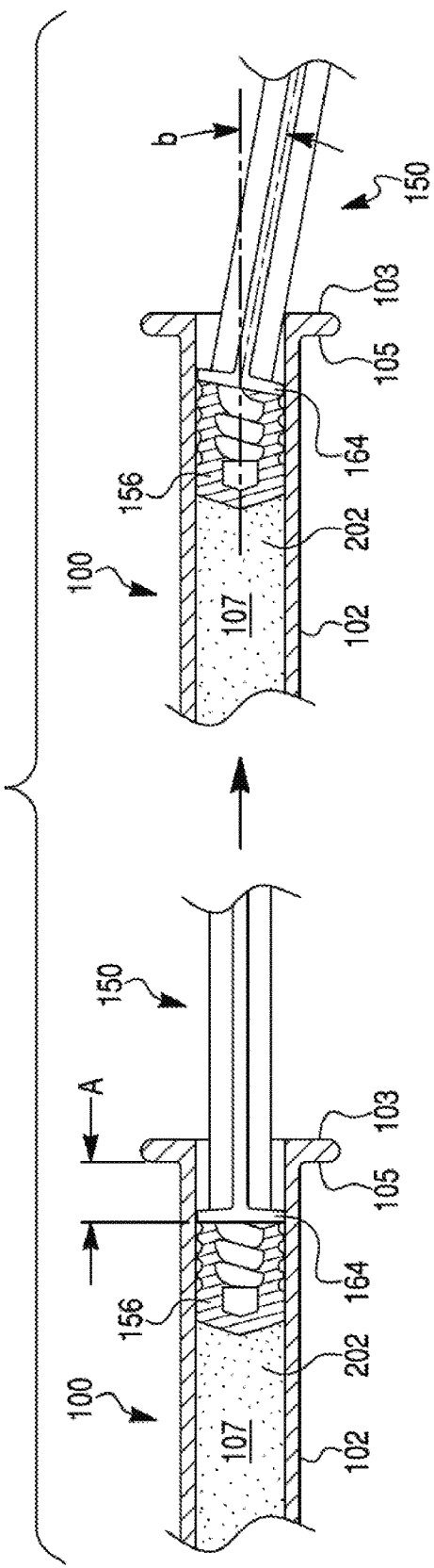

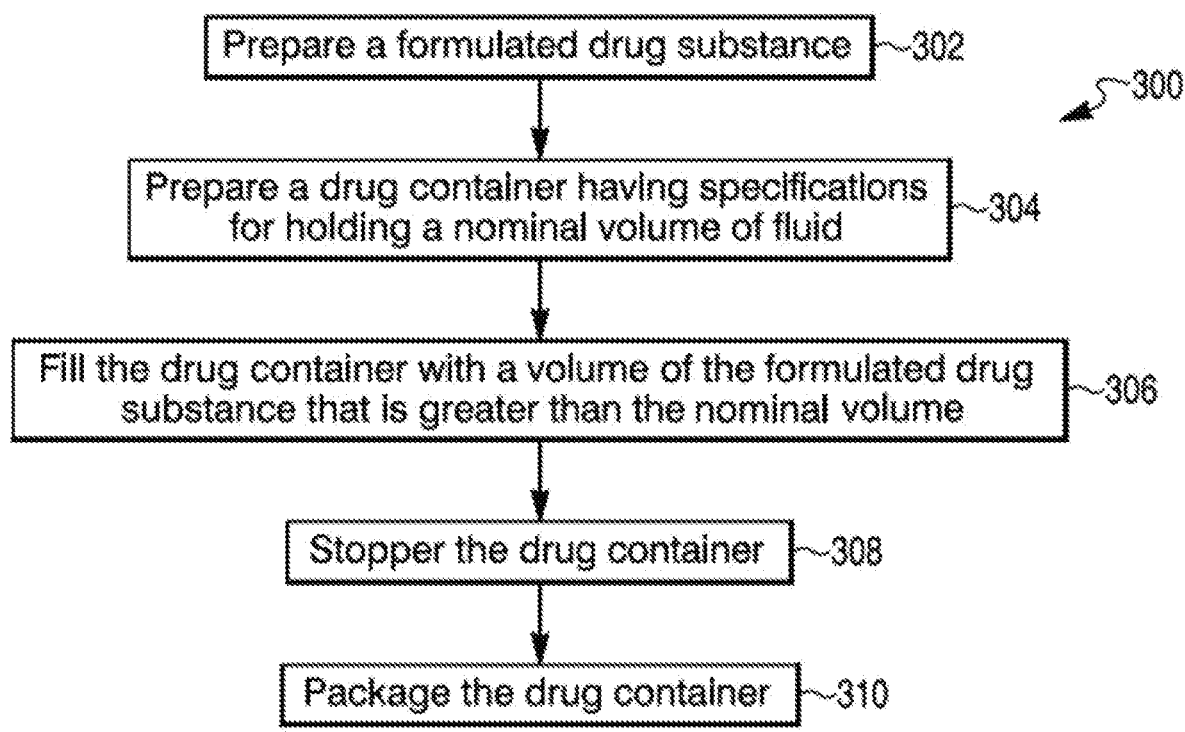

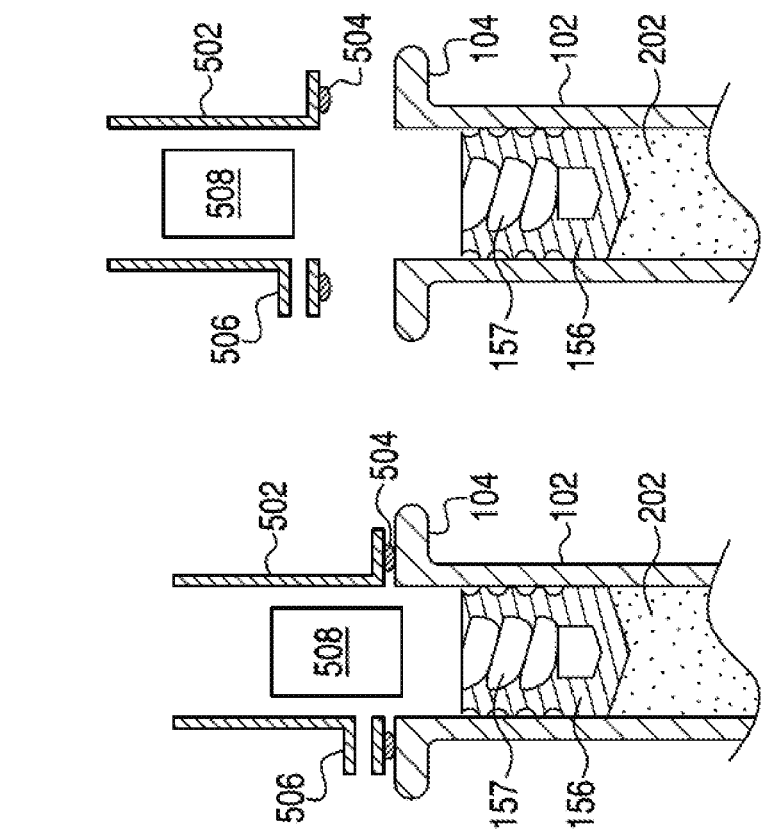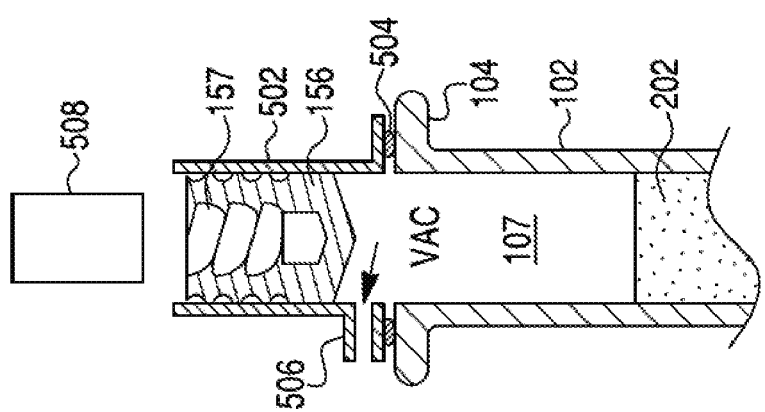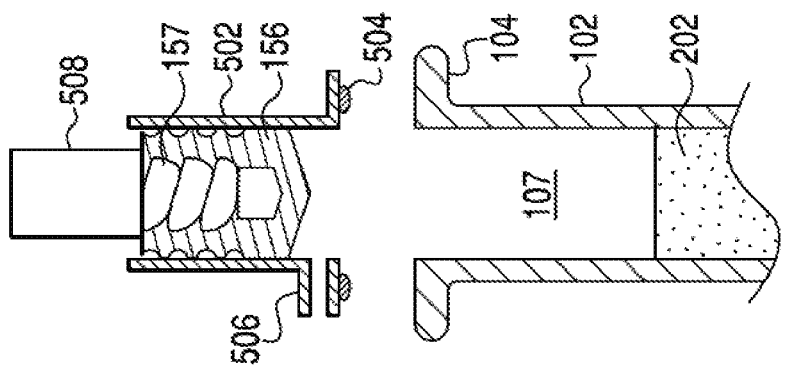
FIG. 5A  FIG. 5B  FIG. 5C  FIG. 5D

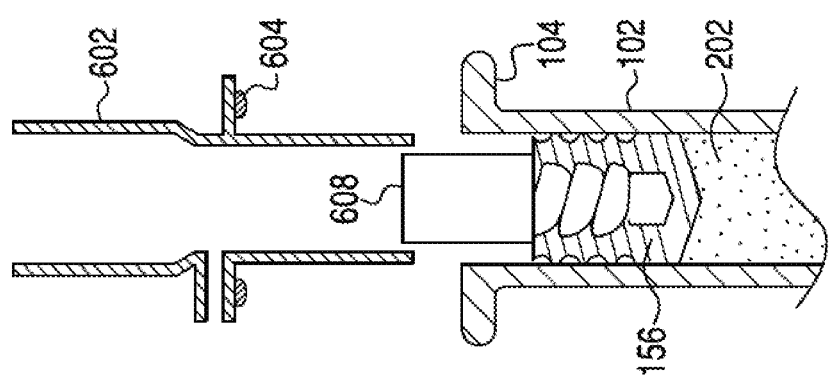
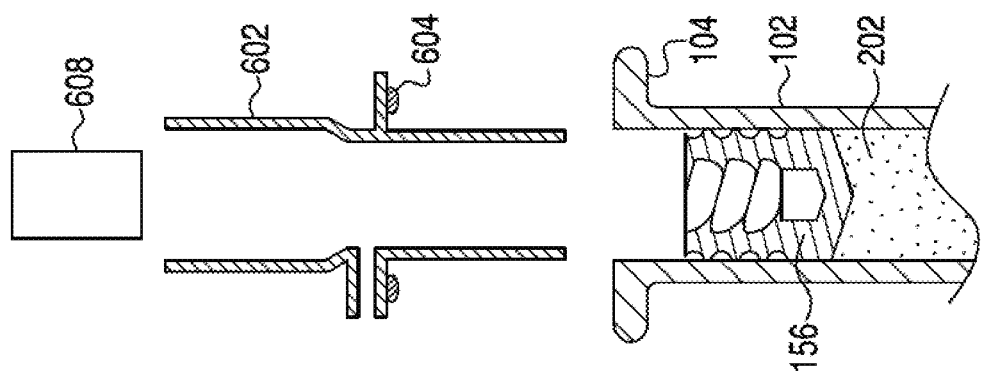

US 11,577,025 B2

DEVICES AND METHODS FOR OVERFILLING DRUG CONTAINERS

CROSS-REFERENCE TO RELATED APPLICATION(S)

This patent application is a 35 U.S.C. § 371 National Phase of International Application No. PCT/US2017/040011, filed Jun. 29, 2017.

FIELD OF THE DISCLOSURE

Various embodiments of the present disclosure relate to devices and methods for overfilling primary packaging components. More specifically, particular embodiments of the present disclosure relate to devices and methods for overfilling syringes, including prefillable syringes.

INTRODUCTION

Primary packaging components, such as syringes, intravenous fluid containers, vials, and other drug containers, are specified to hold a maximum volume of formulated drug product or other fluid. For example, a syringe may be manufactured and sold with a nominal volume, or a maximum volume that the syringe has been tested to hold while still ensuring proper functioning of the syringe's stopper, plunger, and other parts, without compromising the contents or integrity of the stoppered syringe. In particular, a nominal volume of a prefillable syringe may be specified so as to ensure that the syringe, once filled, retains its integrity through various post-filling processes, such as packaging and shipment. In some situations, however, the nominal volume of a primary packaging component may be less than a desired volume of formulated drug substance for inclusion in the primary packaging component, due to, for example, a disparity between the nominal volume of the packaging and a desired dosage volume, or a lack of suitable larger packaging.

SUMMARY

The present disclosure relates to drug products, and methods of their preparation. In particular, the present disclosure relates to overfilling primary packaging components with formulated drug substances.

In an aspect of the present disclosure, there is provided a method of preparing a drug product, comprising introducing a volume of a formulated drug substance into a primary packaging component, wherein the volume of the formulated drug substance is greater than a nominal volume of the primary packaging component, and positioning a stopper within the primary packaging component, wherein positioning the stopper comprises applying a vacuum to the stopper.

In an embodiment, the primary packaging component is a syringe. In a further embodiment, the primary packaging component is a prefillable syringe. In a further embodiment, the primary packaging component is a prefillable syringe having a nominal volume of at least 1 mL. In yet another embodiment, the primary packaging component is a prefillable syringe, the nominal volume is 1 mL, and positioning the stopper within the primary packaging component includes inserting the stopper into a body of the syringe such that an end of the stopper closest to a flange of the syringe is between about 2.5 mm and about 5.0 mm away from the flange of the syringe. In another embodiment, applying the vacuum to the part of the primary packaging component includes subjecting the part of the primary packaging component to a pressure of between 70 and 75 mBar.

In one embodiment, the volume of the formulated drug substance is between 1.05 mL and 1.30 mL. In a further embodiment, the volume of the formulated drug substance is between about 110% and about 140% of the nominal volume of the primary packaging component. In another embodiment, the formulated drug substance is at least 0.05 mL greater than the nominal volume of the primary packaging component. In a further embodiment, the formulated drug substance comprises one of a protein, a nucleic acid, or a gene therapy medicament. In yet another embodiment, the formulated drug substance comprises an antibody and at least one excipient. In another embodiment, the formulated drug substance comprises an antibody solution, wherein the antibody is present in the solution at a concentration of at least 100 mg/mL. In a further embodiment, the formulated drug substances comprises an antibody, and has a viscosity of at least 5 cPoise.

In one embodiment, the method includes placing the primary packaging component into additional packaging. In another embodiment, the method may be repeated for each of a plurality of primary packaging components in a batch. For example, a batch of primary packaging components may comprise 80 prefilled syringes.

In a further aspect of the present disclosure, a drug product is prepared by one of the above-described methods.

In another aspect of the present disclosure, there is provided a method of preparing a drug product, comprising introducing a volume of a formulated drug substance into a prefillable syringe, the formulated drug substance comprising an antibody, wherein the volume of the formulated drug substance is greater than a nominal volume of the prefillable syringe, and stoppering the prefillable syringe using one of a vacuum stoppering process or a vacuum-assisted stoppering process.

In another aspect, there is provided a drug product, comprising a primary packaging component having a nominal volume, a volume of formulated drug substance in the primary packaging component, wherein the volume of formulated drug substance is greater than the nominal volume, and a stopper. In an embodiment of this aspect, the primary packaging component is a prefillable syringe. In a further embodiment, the prefillable syringe has a body and a flange surrounding an opening in the body, and a minimum distance between the flange and the stopper is at least 2.5 mm. In yet another embodiment, the nominal volume is 1 mL, and the volume of formulated drug substance is at least 1.05 mL. In another embodiment, the formulated drug substance comprises a protein, a nucleic acid, a blood component, a vaccine, an anti-allergenic, a gene therapy medicament, an antibiotic, a pain management medication, an anesthetic, and/or a hormone. In a further embodiment, the formulated drug substance comprises an antibody.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

FIG. 3A is a schematic drawing of an exemplary overfilled and stoppered primary packaging component, according to the present disclosure.

FIG. 3B is another schematic drawing of an exemplary overfilled and stoppered primary packaging component, according to the present disclosure.

FIGS. 3C and 3D are partial schematic drawings of stoppered primary packaging components, according to the present disclosure.

FIG. 4 is a flow diagram of an exemplary method for overfilling a primary packaging component, according to the present disclosure.

FIGS. 5A-5D are schematic drawings of steps in an exemplary process of stoppering an overfilled primary packaging component.

FIGS. 6A-6E are schematic drawings of steps in another exemplary process of stoppering an overfilled primary packaging component.

Figure 1A:
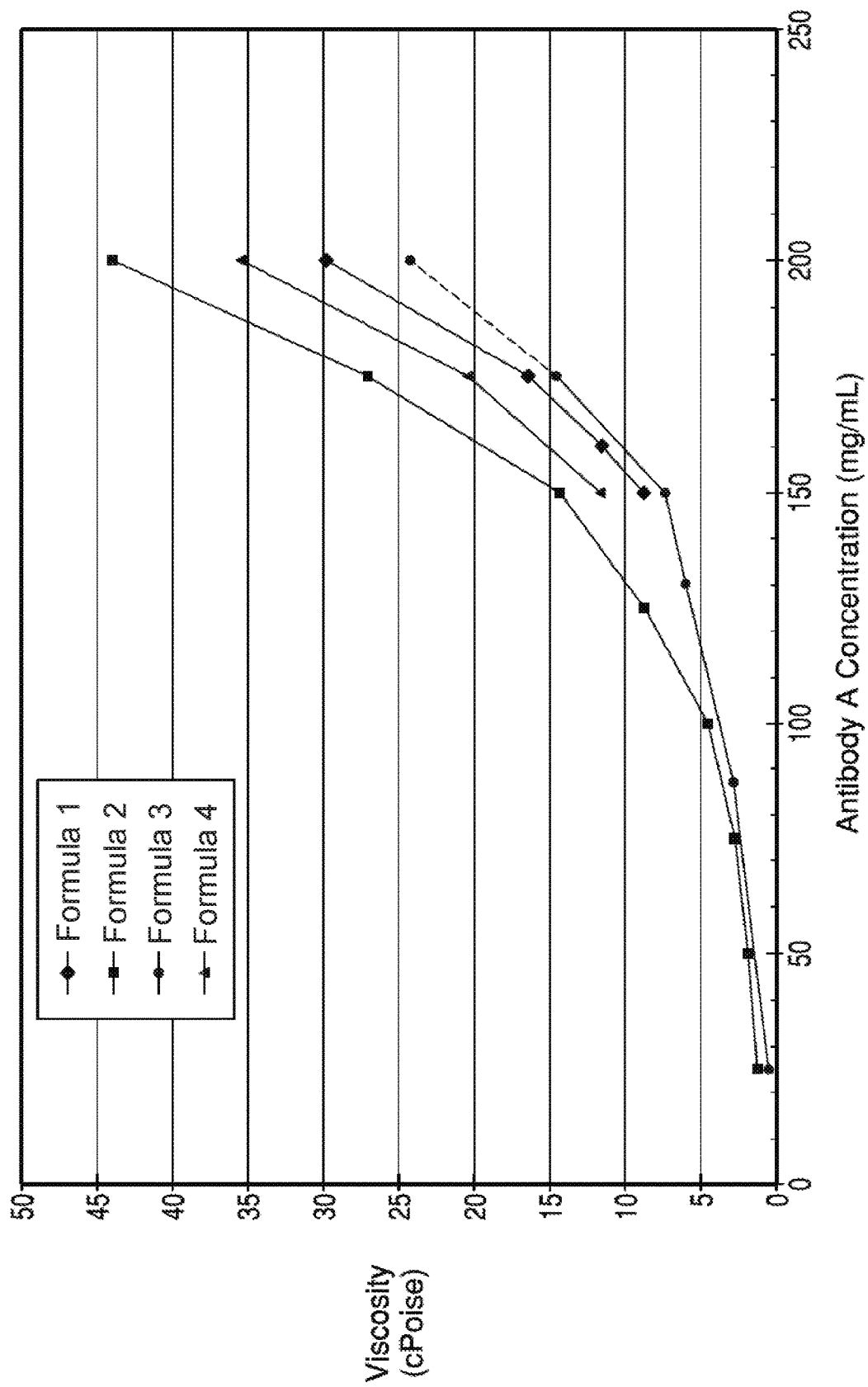
FIGS. 1A and 1B are graphs showing viscosities of exemplary antibody solutions as a function of antibody concentration, formulation, and temperature.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items.

DETAILED DESCRIPTION

Embodiments of the present disclosure relate to systems and methods for overfilling primary packaging components. For example, embodiments of the present disclosure may relate to systems and methods for overfilling drug containers, such as syringes. More particularly, embodiments of the present disclosure may relate to, e.g., systems and methods for overfilling prefillable syringes ("PFS") for packaging, sale, and commercial use. "Overfilling" in the context of the present disclosure refers to filling of a container with a larger volume of a substance than the nominal volume of the container, while still maintaining a desired level of safety and/or integrity as to the container and its contents.

The "nominal volume" (also called the "specified volume," or "specified capacity") of a container refers to the container's maximum capacity, as identified by the container's manufacturer or a safety standards organization. A manufacturer or a safety standards organization may specify a container's nominal volume to indicate that the container can be filled with that volume of fluid (either aseptically or not) and be closed, stoppered, sterilized, packaged, transported, and/or used while maintaining container closure integrity, and while maintaining the safety, sterility, and/or aseptic nature of the fluid contained inside. In determining the nominal volume of a container, a manufacturer or a safety standards organization may also take into account variability that occurs during normal filling, closing, stoppering, packaging, transportation, and administration procedures. As an example, a prefillable syringe may be either hand- or machine-filled with up to its nominal volume of fluid, and may then be either vent tube- or vacuum-stoppered, without the filling and stoppering machinery and tools touching and potentially contaminating the contents of the syringe.

Overfilling a container may include filling the container with more than its nominal volume of fluid. For example, overfilling a PFS having a nominal volume of 1 mL of fluid may include filling a barrel of the PFS with more than 1 mL of fluid and stoppering the PFS such that the stopper is unlikely to be moved, dislodged, or otherwise compromised during routine packaging, transport, or administration, as will be discussed in greater detail below.

The term "formulated drug substance" refers to a substance including a therapeutic ingredient (e.g., an active pharmaceutical ingredient such as a biologic or a traditional pharmaceutical chemical) and one or more excipients and diluents. The term "drug product," as used herein, may refer to a volume of a formulated drug substance apportioned into a primary packaging component for packaging, transportation, delivery, and/or administration to a patient.

The term "primary packaging component" refers to a packaging component for a drug, such as a drug container, that is designed and manufactured to be in direct physical contact with the formulated drug substance. (See, for example, Guidance for Industry on Container Closure Systems for Packaging Human Drugs and Biologics, U.S. Department of Health and Human Services, Food and Drug Administration, Center for Drug Evaluation and Research, and Center for Biologics Evaluation and Research (May 1999), which is incorporated by reference herein.) Examples of primary packaging components include prefillable syringes, Luer syringes, cartridges, and vials made of glass, plastic, and/or other materials.

Figure 1B:
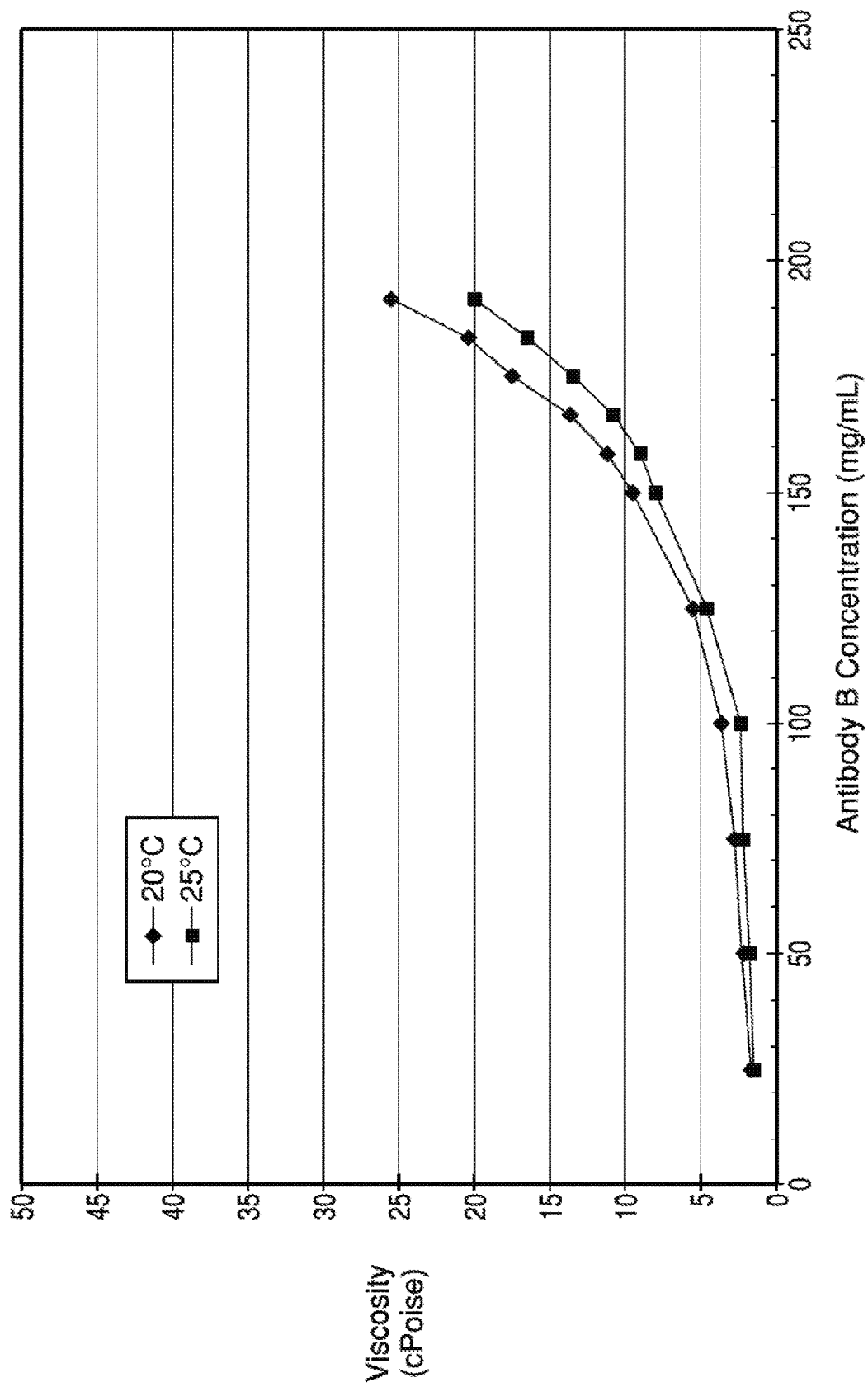

It is generally desired that a primary packaging component in which a formulated drug substance is packaged (e.g., in an aseptic filling process or a non-aseptic filling process), sterilized, sold, and/or used be able to contain a suitable or desired amount of the formulated drug substance for use (such as, for example, a single dose of the formulated drug substance), while also being able to withstand packaging processes, transportation, and use while remaining secure and closed, maintaining structural integrity and sterility (e.g., aseptic conditions), remaining safe for handling by medical professionals, patients, and others, and protecting the formulated drug substance from risk of damage or unwanted alteration. Often, standardized or mass-produced packaging components may have standard or commonly-used nominal volumes, such as 0.5 mL, 1 mL, 1.5 mL, 2 mL, 2.25 mL, 2.5 mL, 3 mL, 5 mL, etc. The desired or suitable volume of a formulated drug substance, however, may vary beyond these quantities (e.g., volumes between 0.5 mL and 1 mL, 1 mL and 2 mL, or 2 mL and 3 mL), based on factors such as prescribed dosage amount, solubility of an active ingredient in a liquid dosage form, and other factors. For example, increasing the concentration of an active ingredient in a liquid dosage form may impact the short- and long-term stability and solubility of the active ingredient in solution. Increasing the concentration of some active ingredients (e.g., antibodies) may also increase the viscosity of the liquid to an undesirable level, such as a level that cannot easily be administered from a device (such as injection from a syringe) or that is unsuitable for a patient's body. For example, FIGS. 1A and 1B depict plots of the viscosity of two exemplary liquid antibody formulations. In particular, FIG. 1A depicts a plot of the viscosities of four different formulations of an Antibody A as a function of antibody concentration. FIG. 1B depicts a plot of the viscosities of a formulation of an Antibody B as a function of antibody concentration, at two different temperatures (20° C. and 25° C.). As shown in FIGS. 1A-1B, the viscosity of each formulation increases exponentially in relation to increases in antibody concentration. Thus, as demonstrated by these exemplary formulations, even slight increases to the concentration of an antibody in a composition may have a proportionally large effect (e.g., an exponentially larger effect) on the composition's viscosity and suitability for loading into a delivery device or administering to a patient.

In some cases, in order to deliver a desired dose, a volume of a formulated drug substance for inclusion in a drug product may be slightly more than the nominal volume of the drug product's primary packaging component (e.g., the desired volume of formulated drug substance may be 1.1 mL or 1.2 mL, and a drug product's primary packaging component may have a nominal volume of only 1 mL). This may occur for a variety of reasons. For example, research on an active ingredient may reveal that a particular dose of the active ingredient may be efficacious or beneficial for treatment of a disease state, but the particular dose may not be deliverable using only the nominal volume of a primary packaging component, because including that particular dose of active ingredient in a volume of liquid equal to the nominal volume of the primary packaging component might increase the viscosity of the drug product to an undesirable level (as described above). As another example, a concentration of a desired dose of active ingredient in a nominal volume of fluid may be too high to be safe or effective in treating a patient (i.e., a lower concentration is needed for safety, efficacy, or regulatory standards). Thus, it may be practicable, desirable, or necessary to add a higher volume of formulated drug substance into a drug product, beyond a nominal volume of the drug product's primary packaging component, instead of increasing the concentration of the active ingredient in the formulated drug substance and keeping the total volume of formulated drug substance in the drug product lower (i.e., at or below a nominal volume of the primary packaging component).

In addition, it may be desirable to fit more formulated drug substance into a primary packaging component with a nominal volume that is close to, but slightly less than, the desired volume of the formulated drug substance, instead of either using a single drug container having a larger nominal volume, or using two smaller drug containers having smaller nominal volumes. For example, it may be desirable to package 1.2 mL of a formulated drug substance in a single primary packaging component having a nominal volume of 1.0 mL, instead of a primary packaging component having a nominal volume of 1.5 mL or 2.0 mL, or splitting the 1.2 mL of formulated drug substance in between two primary packaging components each having a nominal volume of 1.0 mL. This may be for a number of reasons. For example:

A primary packaging component with a nominal volume that is the exact same as, or larger than, a desired volume of formulated drug substance for inclusion in a drug product may not be readily available. For example, a particular type of syringe, such as a ready-to-fill syringe or a staked needle syringe, may not be available in sizes having nominal volumes equal to or larger than a desired volume of a formulated drug substance. In particular, some types of primary packaging components historically have been produced with limited small nominal volumes. For example, some types of syringes have historically been produced with nominal volumes of 1 mL or less. Manufacturing tooling, packaging, sterilization equipment and processes, and delivery devices (e.g., autoinjectors) for these syringes, likewise may have been be designed for a limited range of syringe sizes.

In some cases, a regulatory administration (such as the U.S. Food and Drug Administration) may clear delivery of a drug in a particular size of primary packaging component, but not in other sizes of primary packaging components.

Using a primary packaging component with a nominal volume larger than the desired volume of the formulated drug substance may result in too much "dead" or empty air space within the packaging, which in turn may result in unwanted exposure of the formulated drug substance to air, unwanted agitation and creation of bubbles in the packaging, and/or other complications;

Using a primary packaging component with a nominal volume larger than the desired volume of the formulated drug substance may result in higher packing and shipment costs;

A drug product designed to be portable may become less portable if it is in a packaging component having a larger size than is necessary;

Patients who self-administer a parenteral drug product may be more averse to injecting themselves with a larger syringe than a smaller one;

Drug products designed to be administered multiple times (e.g., on a twice-daily schedule) may result in lower patient compliance as compared to drug products designed to be administered fewer times, such as once daily;

A primary packaging component designed to function with other devices (e.g., a secondary packaging component, such as an auto-injector, a pen, a needle cover, or a safety device) may be less compatible with those devices if it changes in size; and/or Primary packaging components with nominal volumes slightly smaller than the desired volume of formulated drug substance may be less expensive or more readily available at the time that filling is taking place.

For any or all of these reasons, it may be desirable to deliver an increased volume of a formulated drug substance in a primary packaging component (such as a syringe) with a smaller nominal volume, e.g., to allow for an increase in active ingredient dosage, while maintaining tolerable viscosity levels, without necessitating the use of new manufacturing, tooling, packaging, sterilization, and/or delivery processes and/or devices (or even new regulatory clearances).

Several consequences of overfilling primary packaging components may, however, affect the safety, efficacy, efficiency, sterility, and other aspects of the primary packaging components and/or the drug substances contained therein. For example, added volume of formulated drug substance in a primary packaging component (e.g., a syringe) may affect the extent to which the primary packaging component may be securely stoppered and handled during packaging, shipping, delivery, and administration.

Systems and methods disclosed herein may advantageously be used to successfully overfill primary packaging components, such that the packaging components are filled with a volume of a formulated drug substance greater than their nominal volume, while maintaining desired closure and integrity of the primary packaging components and their contents. Specifically, systems and methods disclosed herein may advantageously be used in successfully overfilling PFS. For example, systems and methods disclosed herein may be used in successfully overfilling PFS with a variety of liquid or fluid formulated drug substances for parenteral administration, including formulated drug substances having active ingredients such as antibodies, vaccines, antibiotics, pain management medications, anesthetics, hormones, proteins, small molecules, and any other liquid or fluid formulated drug substances. While aspects of the present disclosure are described in terms of overfilling a PFS with a liquid, it is to be understood that the systems and methods disclosed herein may apply to overfilling a variety of primary packaging components with a variety of types of fluids. In addition, though the present disclosure makes reference to overfilling a PFS with a formulated drug substance including a biologic (e.g., an antibody such as a human monoclonal antibody, a glycosylated protein or other protein, a nucleic acid, a gene therapy medicament, or post-translational molecule), those of ordinary skill in the art will readily recognize that aspects of the present disclosure contemplate overfilling a PFS with any formulated drug substance, such as one including any blood component, vaccine, anti-allergenic, antibiotic, pain management medication, anesthetic, hormone, and/or small molecule.

Figure 2A:
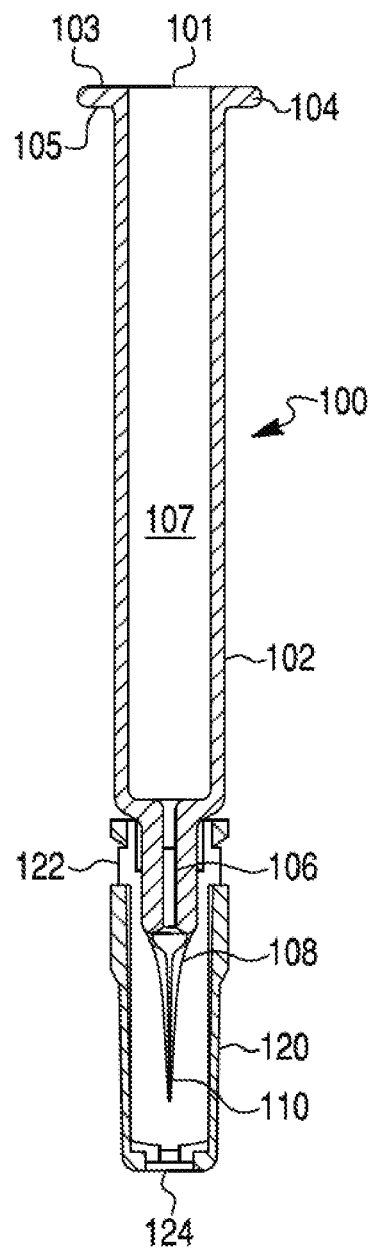
FIGS. 2A and 2B are schematic drawings of components of an exemplary primary packaging component suitable for overfilling, according to the present disclosure.

FIG. 2A depicts in schematic form an exemplary staked syringe 100, which may be overfilled according to the present disclosure. Parts of syringe 100 are depicted in cross-sectional form. Syringe 100 may include a body 102, which may have a flange 104 surrounding an opening at a proximal end of the syringe 100 and a passage 106 leading to a needle 110, at a distal end of the syringe 100. Needle 110 may be covered by a sheath 108. Syringe 100 may also include a cap 120, which may cover the needle 110. Cap 120 may include a grip 122 and a reinforced tip 124.

Syringe 100 may be any type of syringe having a nominal volume for parenteral administration of a formulated drug substance, such as a standard syringe or a long syringe. For example, syringe 100 may be a PFS suitable for sterilizing, pre-filling, packaging, shipping, and single-use administration. Syringe 100 may be made of any suitable material or combination of materials, such as, for example, glass, plastic, and/or metal. Syringe 100 may have any nominal volume, such as, for example, 0.3 mL, 0.5 mL, 1 mL, 1.5 mL, 2 mL, 2.25 mL, 2.5 mL, 3 mL, 5 mL, or any other nominal volume. For example, syringe 100 may be an Ompi EZ-fill® syringe, a Gerresheimer ready-to-fill syringe, a BD Hypak SCF™ syringe, or other bulk-processed ready-to-fill or prefillable syringe. Syringe 100, however, may have capacity to physically hold more than its nominal volume in fluid. In some embodiments, syringe 100 may be a multi-use syringe. In some embodiments, syringe 100 may be suitable for loading into an auto-injector.

Body 102 of syringe 100 may be configured to hold at least the nominal volume of syringe 100 in fluid. Body 102 may be cylindrical, or may have any other suitable shape, such as an elliptic cylinder or a rectangular prism. Body 102 may be made of any suitable material for holding a formulated drug substance, such as glass, plastic, metal, and/or silicone. Body 102 may also have a wall thickness suitable for maintaining integrity through various handling procedures, such as sterilization, filling, stoppering, packaging, shipment, and/or use. Body 102 may have an opening 101 at its proximal end, through which a fluid and a stopper assembly (e.g., stopper assembly 150 depicted in FIG. 2B) may be introduced into an interior 107 of body 102. Interior 107 may have a substantially constant cross-sectional size and shape throughout body 102, such that, for example, a stopper may remain in contact with an interior surface of the walls of body 102 while being moved through interior 107. In some embodiments, body 102 may be transparent, such that any contents placed within body 102 may be visible through the walls of body 102.

Flange 104 may surround opening 101 at the proximal end of body 102. Flange 104 may have a proximal side 103 and a distal side 105. In some embodiments, flange 104 may be configured to allow for grip around distal side 105 (for example, a finger grip or a mechanical grip), and/or for a plunger flange (e.g., plunger flange 154 depicted in FIG. 2B) to rest against proximal side 103 when a plunger is pushed fully into body 102. Depending on the length of plunger rod 152, flange 104 may serve to limit an insertion distance of plunger 150 into body 107. Flange 104 may have an oval profile, a circular profile, or may be a clipped flange.

Passage 106 may connect body 102 with needle 110. In some embodiments, passage 106 may be substantially narrower than interior 107, so as to reduce the volume or flow of fluid that may be pushed toward needle 110. Needle 110 may be fluidly connected to passage 106, such that fluid may pass from body 102, through passage 106 and through needle 110. The connection between needle 110 and passage 106 may be any suitable connection known in the art. Needle 110 may have an opening (not pictured) in or near its distal end, through which fluid may be ejected. Needle 110 may be of any suitable biocompatible material for injection into tissue, such as stainless steel, titanium, or any other metal. Sheath 108 may cover needle 110 in order to, for example, protect the tip of needle 110 and/or prevent fluid from leaking out of needle 110.

Cap 120 may be sized and configured to cover needle 110 and secure to body 102 and/or sheath 108. Cap 120 may be made of any material suitable to protect needle 110, such as, for example, rubber, glass, plastic, thermoplastic elastomer, other polymer, metal, or combination of such materials. Cap 120 may be securable to body 102 in any known removable manner, such as by a threaded connection, or other interlocking connection. Cap 120 may include, for example, a grip 122 to allow for ease of removal of cap 120.

Figure 2B:
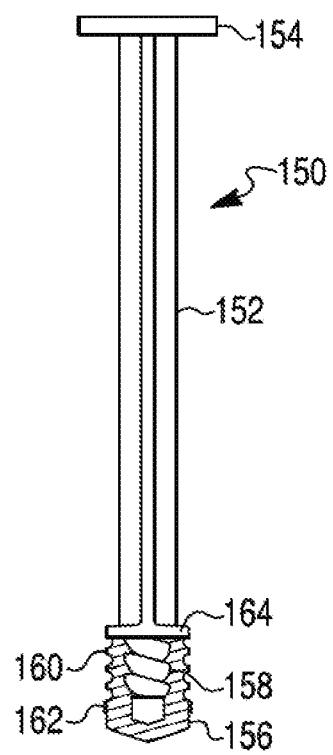

FIG. 2B depicts in schematic form an exemplary stopper assembly 150. Stopper assembly 150 may include a plunger rod 152 and plunger flange 154. Stopper assembly 150 may also include a stopper 156 (depicted in cross-sectional form), which may be connected to plunger rod 152 via a connector 158. Stopper 156 may also include circumferential ribbing 160, one or more protrusions 162, and a top 164.

Stopper assembly 150 may be compatible (e.g., appropriately sized) with syringe 100, such that plunger rod 152 and stopper 156 fit snugly into body 102 of syringe 100. Plunger rod 152 and stopper 156 may also be compatible with one another, such that stopper 156 may be securely joined to plunger rod 152 via, for example, connector 158. In some embodiments, plunger rod 152 and stopper 156 may be manufactured specifically to be compatible with one another. For example, if syringe 100 is a 1 mL syringe (e.g., either a standard or long syringe), then plunger rod 152 may be a corresponding 1 mL plunger rod, and stopper 156 may be a corresponding 1 mL stopper, such as a fluoropolymer-coated stopper. In some embodiments, stopper 156 may be manufactured to be insertable into interior 107 of body 102 before being connected to plunger rod 152, after which plunger rod 152 may be connected into the inserted stopper 156 by connector 158. In embodiments where connector 158 is a screw connector, for example, stopper 156 may have a cavity that is threaded in a manner complementary to a helical screw shape of connector 158, into which connector 158 may be screwed.

Plunger rod 152 may be sized and configured to pull and push stopper 156 through interior 107 of body 102, once connected to stopper 156 via connecter 158. Plunger rod 152 may thus be made of any material suitable to withstand the force necessary to move stopper 156 through interior 107 of body 102. For example, plunger rod 152 may be made of metal, glass, plastic, other polymer, or a combination thereof. Stopper 156 may likewise be sized and configured to fit snugly within interior 107. For example, if interior 107 has a substantially constant circular cross section (i.e., if body 102 is cylindrical), stopper 156 may likewise have a circular cross section with a diameter designed to fit snugly within a diameter of interior 107. Stopper 156 may be made of any suitable material known in the art, such as, for example, rubber, plastic, silicone, or thermoplastic elastomer. In some embodiments, stopper 156 may be coated with a material that reduces interaction between the material of stopper 156 and a formulated drug substance housed within body 102. For example, stopper 156 may be coated in a Teflon or fluoropolymer film, or in a bonded silicone oil. Additionally, stopper 156 may have circumferential ribbing 160 and/or one or more protrusions 162, which may be configured to increase a seal between stopper 156 and body 102, without preventing movability of stopper 156 in body 102.

FIG. 3A depicts in schematic form a filled and stoppered syringe assembly 200, including stopper assembly 150 inserted into syringe 100, such that stopper 156 and a part of plunger rod 152 are inside body 102 to where top 164 of stopper 156 is inserted past distal side 105 of flange 104 by a distance A. Syringe assembly 200 is filled with a formulated drug substance 202.

Formulated drug substance 202 may be any fluid formulated drug substance suitable for packaging within syringe assembly 200. For example, formulated drug substance 202 may be any fluid suitable for parenteral administration through needle 110. Formulated drug substance 202 may be, for example, a liquid, a gel, or a suspension. In some embodiments, formulated drug substance 202 may include an active pharmaceutical ingredient (API) in a liquid or gel solution. Such an API may be any suitable API for therapeutic administration, such as a protein (e.g., an antibody such as a human monoclonal antibody, a glycosylated protein, or other protein), a nucleic acid, a gene therapy medicament, an antibiotic, a pain management medication, an anesthetic, a hormone, or other large- or small-molecule API.

In some embodiments, a volume of formulated drug substance 202 introduced into syringe 100 may be greater than a nominal volume of syringe 100. For example, in some embodiments, a volume of formulated drug substance 202 may be at least about 3% greater than a nominal volume of syringe 100. In some embodiments, a volume of formulated drug substance 202 may be between about 3% and about 40% greater than a nominal volume of syringe 100. In some embodiments, a volume of formulated drug substance 202 may be between about 3% and about 30%, between about 12% and about 25%, or between about 14% and about 25% greater than a nominal volume of syringe 100. In some embodiments, a volume of formulated drug substance 202 may be about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% greater than a nominal volume of syringe 100. In further embodiments, a volume of formulated drug substance 202 may be between about 0.1 mL and 0.3 mL greater than a nominal volume of syringe 100. For example, in a syringe having a nominal volume of 1 mL, a volume of formulated drug substance 202 may be between about 1.09 mL and 1.30 mL, such as between about 1.10 mL and 1.27 mL, 1.10 mL and 1.25 mL, or 1.10 mL and 1.15 mL, such as 1.09 mL, 1.10 mL, 1.11 mL, 1.12 mL, 1.13 mL, 1.14 mL, 1.15 mL, 1.16 mL, 1.17 mL, 1.18 mL, 1.19 mL, 1.20 mL, 1.21 mL, 1.22 mL, 1.23 mL, 1.24 mL, 1.25 mL, 1.26 mL, or 1.27 mL. As another example, in a syringe having a nominal volume of 2 mL, a volume of formulated drug substance 202 may be between about 2.09 mL and 2.30 mL, such as between about 2.10 mL and 2.25 mL, 2.10 mL and 2.20 mL, or 2.10 mL and 2.15 mL, such as 2.09 mL, 2.10 mL, 2.11 mL, 2.12 mL, 2.13 mL, 2.14 mL, 2.15 mL, 2.16 mL, 2.17 mL, 2.18 mL, 2.19 mL, or 2.20 mL. In some embodiments, a volume of formulated drug substance 202 may be greater than a nominal volume of syringe 100 but less than 140%, 130%, or 120% of the nominal volume of syringe 100.

In some embodiments, the volume of formulated drug substance 202 introduced into syringe 100 may be slightly greater than the volume of formulated drug substance 202 that may be expelled from syringe 100 through needle 110, due to "dead volume," e.g., volume that remains trapped in passage 106 (and/or needle 110) after stopper assembly 150 has been fully pushed through body 102. For example, in a syringe having a nominal volume of 1 mL, a fill volume of formulated drug substance 202 may be 1.19 mL, but a potential expulsion volume, or administered volume, of formulated drug substance 202 through needle 110 may be about 1.14 mL. In further embodiments, the volume of formulated drug substance 202 introduced into syringe 100 may be greater than the combination of the target volume of formulated drug substance 202 and the dead volume of syringe 100. Additionally, in some embodiments, a target volume of formulated drug substance 202 introduced into syringe 100 may be slightly greater than the target volume of formulated drug substance 202 to be expelled through needle 110, in order to account for variability in filling processes and to guarantee that a minimum amount of formulated drug substance 202 is delivered.

In some embodiments, no air space exists in interior 107 of body 102 after formulated drug substance 202 has been added and stopper 156 has been housed within body 102. In further embodiments, some such air space may exist. For example, in a syringe having a nominal volume of 1 mL, such air space, as measured from any point on the bottom of stopper 156 to any point on a dose line of formulated drug substance 202, may be between about 0.01 mm and about 1 mm. In some embodiments, the existing air space may be relatively small such that an air bubble only may be visible if body 102 is turned on its side, as shown by air bubble 170 in FIG. 3B. In some embodiments, the existing air space may account for between about 5 and 250 µL of fluid volume, such as 150 µL of fluid volume.

Distance A may be a distance from the distal side 105 of flange 104 to top 164 of stopper 156, or from opening 101 at the proximal end of body 102, to top 164 of stopper 156. In some embodiments, distance A may be greater than 0, such that the entirety of stopper 156 is housed within body 102. This may ensure that formulated drug substance 202 is fully sealed within body 102. In further embodiments, distance A may be greater than an experimentally-determined threshold. For example, in some syringes having a nominal volume of 1 mL, distance A may be at least about 1 mm. In some embodiments, distance A may be at least about 1.5 mm, 2 mm, 2.5 mm, at least about 2.56 mm, at least about 2.57 mm, at least about 3 mm, at least about 3.5 mm, at least about 4 mm, at least about 4.5 mm, at least about 5.0 mm, or at least about 5.5 mm.

In some embodiments, distance A may be experimentally determined in part based on an extent to which plunger rod 152 may be able to tilt relative to a longitudinal axis of body 102 in syringe assembly 200. This may be to prevent excess tilting of plunger rod 152 from dislodging stopper 156, thus breaking a sterile seal between stopper 156 and body 102, or otherwise compromise integrity of stopper 156, body 102, and/or syringe assembly 200 (e.g., during packaging, transportation, unpacking, or use of syringe assembly 200). In some embodiments, distance A may be large enough such that any tilting of plunger rod 152 is limited by contact with the wall of body 102, to less than a given angle relative to a longitudinal axis of body 102.

FIGS. 3C and 3D depict alternative placements of stopper 156 in interior 107 of body 102. In FIG. 3C, distance A is too small, because plunger rod 152 may tilt to such an extent (e.g., angle a) that stopper 156 may pull away from the wall of body 102 or may be dislodged from the syringe, thus compromising the integrity of stopper 156 and sterility of stopper 156, syringe 102, and formulated drug substance 202. In FIG. 3D, distance A is adequate, such that tilting of plunger rod 152 is limited by the walls of body 102 (e.g., to an angle b) and is not sufficient to allow stopper 156 to pull away from the wall of body 102 and become dislodged or otherwise compromised. In some embodiments, with certain syringes having a nominal volume of 1 mL, for example, angle $b$ may be no greater than, e.g., 20°, 15°, 12°, or 10°.

An overfilled and stoppered primary packaging component, such as an overfilled and stoppered syringe, may be achieved by a variety of methods. Additionally, a variety of methods may be used in order to package an overfilled and stoppered drug container.

FIG. 4 depicts a flow diagram of steps in a method 300 for overfilling a primary packaging component, such as a drug container. According to step 302, a formulated drug substance may be prepared. According to step 304, a drug container having specifications for holding a nominal volume may be prepared. According to step 306, the drug container may be filled with a volume of formulated drug substance, where the fill volume is greater than the nominal volume. According to step 308, the drug container may be stoppered. According to step 310, the drug container may be packaged.

According to step 302, a formulated drug substance may be prepared. Depending on the formulated drug substance being used (e.g., formulated drug substance 202 depicted in FIGS. 3A and 3B), a variety of preparations may be appropriate. For example, an API may be prepared in a fluid (e.g., liquid or gel) solution suitable for administration to a patient. In some embodiments, an API may be thus prepared so as to avoid precipitation of the API out of solution. As a further example, a pre-made, frozen, and stored formulated drug substance may be removed from storage and thawed to an appropriate temperature for filling, such as room temperature. As another example, a drug substance may be diluted by various excipients and/or buffers to arrive at a formulated drug substance. As yet a further example, a formulated drug substance may be filtered through a filtration system, e.g., to ensure sterility, prior to filling of the drug container. Filtering the formulated drug substance through a filtration system may include one or more of thawing, pooling, mixing, equilibrating temperature of, filtering, and/or transferring the formulated drug substance.

According to step 304, a drug container having a nominal volume may be prepared. For example, syringe assembly 200 depicted in FIGS. 3A and 3B may be disassembled such that syringe 100 is separated from stopper assembly 150. In some embodiments, the drug container may be assembled, removed from packaging, cleaned, or sterilized. In some embodiments, the drug container may be loaded into a filling machine suitable for automatically filling the drug container with a volume of formulated drug substance. As has been previously described with respect to syringe 100 depicted in FIG. 2A, the drug container may have any nominal volume. In some embodiments, multiple drug containers may be assembled and sterilized in bulk, e.g., in batches of 80, 100, 160, 200, or more drug containers.

According to step 306, the drug container may be filled with a volume of the formulated drug substance, where the volume is greater than the nominal volume of the drug container. This filling step may be accomplished by, for example, a machine filling process using an automatic filling machine, using a semi-automatic filling machine, or may be accomplished manually. In some embodiments, the drug container may be filled under vacuum, to prevent volume within the drug container from being taken up by air pockets or bubbles. In some embodiments, multiple drug containers may be filled in bulk, using, e.g., an automated fill finish process. For example, batches of 80, 100, 160, 200, or more drug containers may be filled as part of an automated fill process. In some embodiments, the drug container may be filled in aseptic conditions. The volume of prepared formulated drug substance may be any amount that is greater than the nominal volume. For example, the volume of prepared formulated drug substance may be at least about 10% greater than the nominal volume, or may be any other amount greater than the nominal volume, as has been described with respect to formulated drug substance 202 in syringe assembly 200.

According to step 308, the drug container may be stoppered. Stoppering includes ensuring the proper placement of a stoppering element with respect to the rest of the drug container. For example, with respect to syringe assembly 200, stoppering may include ensuring that the top 164 of stopper 156 has at least passed the distal side 105 of flange 104 of body 102, such that stopper 156 is fully within interior 107 of body 102. In some embodiments, stoppering may include ensuring that the top 164 of stopper 156 is inserted at least a desired distance past distal side 105 of flange 104, as has been previously described with respect to syringe assembly 200.

Stoppering according to step 308 may include a vacuum stoppering process, as depicted in FIGS. 5A-5D, or a vacuum-assisted stoppering processes, as depicted in FIGS. 6A-6E. In such embodiments, a vacuum may be applied during stoppering, to prevent or reduce trapping of air in interior 107 of body 102 and to promote insertion of the stopper as far into interior 107 of body 102 as possible. Vacuum stoppering or vacuum-assisted stoppering may promote overfilling of syringe 100, because a vacuum may facilitate replacing air that would normally be trapped in interior 107 of body 102 with additional volume of formulated drug substance 202. A vacuum stoppering process, for example, will allow a stopper to be drawn close to the fluid in the drug container without mechanical stoppering parts coming into contact with the fluid, and without undesirable deformation (e.g., wrinkling or tearing) of a stopper. For these reasons, a vacuum stoppering process or a vacuum-assisted stoppering process may be preferable to, e.g., a mechanical stoppering process, which may not provide these benefits. In other embodiments, stoppering according to step 308 may be accomplished by any other method known in the art.

FIGS. 5A-5D depict one exemplary vacuum stoppering process. In this vacuum stoppering process, a vacuum is applied to the distal side of the drug container, and the stopper is drawn into the container by the vacuum. As depicted in FIGS. 5A-5D, vacuum housing 502 includes a gasket 504, which may surround vacuum housing 502, and a vacuum conduit 506. Vacuum housing 502 may be sized to hold stopper 156, and may have a diameter comparable to a diameter of syringe body 102. Formulated drug substance 202 may have been introduced into syringe body 202. As depicted in FIG. 5A, stopper 156 may be introduced into vacuum housing 502 with the assistance of an insertion rod 508, which may fit into a cavity 157 of stopper 156. As depicted in FIG. 5B, vacuum housing 502, holding stopper 156, may be positioned over syringe body 102, such that gasket 504 is in contact with flange 104 of syringe body 102. Gasket 504 may create a seal between vacuum housing 502 and flange 104 of body 102. A vacuum may be applied to the sealed area beneath stopper 156 (i.e., interior 107 of body 102), via vacuum conduit 506. The vacuum, with the aid of insertion rod 508, allows stopper 156 to be drawn down out of vacuum housing 502 and into body 102, as depicted in FIG. 5C. The vacuum may aid in ensuring that stopper 156 is placed as close to formulated drug substance 202 as possible. Finally, as depicted in FIG. 5D, vacuum housing 502 may be removed.

Figure 6C:
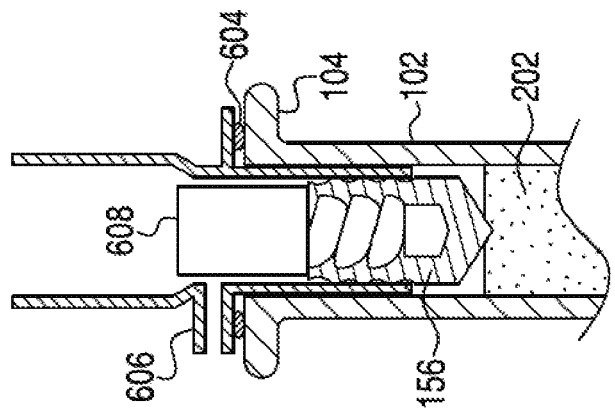
Figure 6B:
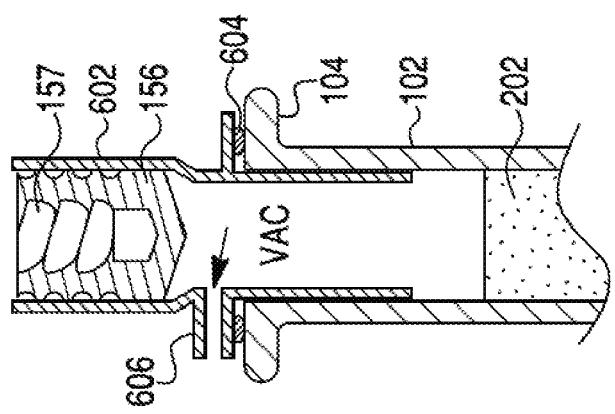
Figure 6A:
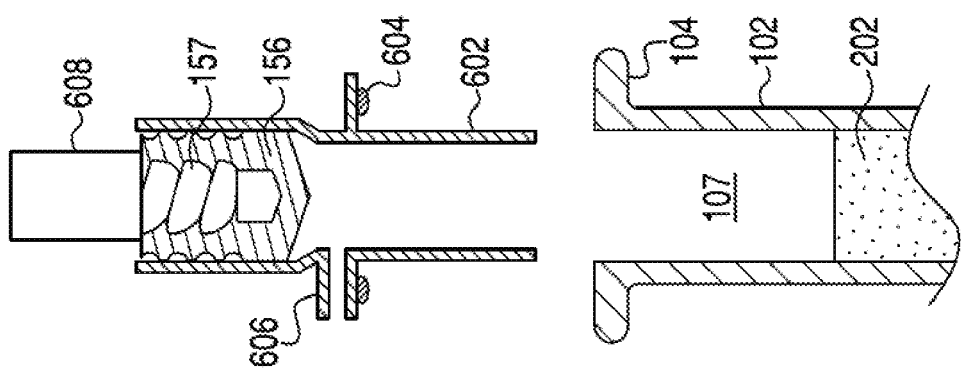

FIGS. 6A-6E depict one exemplary vacuum-assisted stoppering process. In this vacuum-assisted stoppering process, a vacuum is applied to the drug container, and a stopper insertion tube is used to compress the stopper and insert the stopper into the drug container, assisted by the vacuum-created suction. As depicted in FIGS. 6A-6E, stopper insertion tube 602 includes a gasket 604, which may surround stopper insertion tube 602, and a vacuum conduit 606. All or part of stopper insertion tube 602 may be sized to hold stopper 156 in a slightly compressed configuration, and may fit within syringe body 102, into which formulated drug substance 202 has been introduced. As depicted in FIG. 6A, stopper 156 may be introduced into stopper insertion tube 602 with the assistance of an insertion rod 608, which may fit into a cavity 157 of stopper 156. As depicted in FIG. 6B, stopper insertion tube 602, holding stopper 156, may be introduced into interior 107 of syringe body 102. Gasket 604 may create a seal between insertion tube 602 and flange 104 of body 102. A vacuum may be applied to the sealed area beneath stopper 156, via vacuum conduit 606. As depicted in FIG. 6C, insertion rod 608 may be used move stopper 156 through insertion tube 602. The vacuum may assist in further drawing stopper 156 into body 102, such that it is close to formulated drug substance 202. As depicted in FIG. 6D, insertion tube 602 may be removed. Insertion rod 608 may assist in holding stopper 156 in place, such that stopper 156 remains and expands to fit within body 102. As shown in FIG. 6E, insertion rod 608 may be removed. In some embodiments, insertion rod 608 may be removed prior to removal of insertion tube 602, and a vacuum may continue to be applied through insertion tube 602 to draw stopper 156 into body 102 after removal of insertion rod 608.

Using a vacuum or vacuum-assisted stoppering process to draw the stopper into the container may reduce the likelihood that mechanical stoppering elements touch the formulated drug substance within the container, thus preserving the sterility of the formulated drug substance.

In some embodiments, as depicted in FIGS. 5A-5D and 6A-6E, the stoppering element (e.g., stopper 156) may be inserted or drawn into interior 107 of body 102 using a vacuum or vacuum-assisted stoppering process without having a plunger rod (e.g., plunger rod 152) attached. The plunger rod may be connected to the stopper (e.g., via cavity 157) after stoppering is complete.

According to step 310, the drug container may be packaged. Packaging may include, for example, enclosing the entire stoppered drug container in a secondary packaging component (i.e., packaging not in direct contact with the formulated drug substance), such as plastic packaging suitable for shipment of the drug container. Step 310 may also or alternately include applying one or more seals and/or labels to the stoppered drug container or its packaging. In some embodiments, little or no packaging (beyond the drug container) may be necessary.

The stoppered and packaged drug containers may be stored, shipped, and/or used as desired. In some embodiments, the drug containers may be pre-sterilized and filled and stoppered via an aseptic filling process. In further embodiments, the packaged drug container may be "terminally" sterilized. Terminal sterilization may be performed by any method known in the art that does not negatively affect the stoppered drug container by, for example, moving the stopper of the drug container (e.g., stopper 156 in syringe assembly 200) so as to expose the formulated drug substance within the drug container (e.g., formulated drug substance 202 within syringe assembly 200) to a non-sterile environment, or cause the formulated drug substance to leak. Additionally, terminal sterilization may be performed by any method known in the art that does not (i) expose the stoppered drug container and its contents to temperatures and/or pressures that may adversely affect the container or the formulated drug substance inside, or (ii) result in leaching of sterilant residuals from the stopper 156. For example, terminal sterilization may be accomplished by vaporized hydrogen peroxide sterilization processes, such as those disclosed in U.S. Patent Application Nos. 62/477,030, filed on Mar. 27, 2017, and 62/472,067, filed on Mar. 17, 2017, which are incorporated by reference herein. Terminal sterilization may also be accomplished by, for example, other processes using vaporized hydrogen peroxide, ethylene oxide (EO) sterilization, radiation, steam, or nitrogen dioxide ($NO_2$), gamma radiation sterilization, electron beam sterilization, or other processes known in the art.

In some embodiments, any or all of the above-described steps and phases may be executed manually, automatically by various preparation, filling, and stoppering machines and methods known in the art, or by a combination of manual and automatic actions. In some embodiments, any or all of the above-described steps and phases may be executed on one or more batches of drug containers. A batch may include, for example, a plurality of the same drug containers that may be prepared, overfilled, stoppered, etc. in a group. For example, a batch of prefillable syringes may include 10, 50, 80, 150, 160, 200, 1,000, 10,000, 20,000, 50,000, 100,000 or more prefillable syringes. In addition, any of the aforementioned steps of method 300 may be omitted or combined with another step. Furthermore, although some of the above-described steps and phases may be described with regard to drug containers or, more specifically, syringes, it is to be understood that the steps disclosed herein may be applied to a variety of primary packaging components. Moreover, one or more of the aforementioned steps may be performed out of the order depicted in FIG. 4.

EXAMPLES

Example 1

The theoretical feasibility of overfilling a syringe was determined as follows. A 1 mL BD Hypak Physiolys SCF™ low tungsten syringe (Beckton Dickinson Medical) was analyzed in order to determine if it could be filled with 1.15 mL or 1.10 mL administered drug volume when paired with a 1 mL BD Hypak PS Flurotec plunger stopper and a 1 mL BD Hypak 21510 PR C Plunger Rod (Beckton Dickinson Medical).

First, the theoretical fill volumes required to achieve administered drug volumes of 1.15 mL and 1.10 mL were determined. Theoretical lost volumes (e.g., dead volumes, or volumes remaining in the syringe after expulsion of as much volume as possible, and potential negative deviations from desired volumes based on variability in fill processes) were determined based on measurements from drawings of the syringe, calculated fill heights of the desired administered drug volume, and in-process control (IPC) capabilities. These theoretical lost volumes were calculated to be as follows:

TABLE 1

| Parameter | Nominal case | Worst case |
| --- | --- | --- |
| Volume lost due to needle droplet | 0.003 mL | 0.005 mL |
| Volume lost due to syringe dead volume | 0.006 mL | 0.010 mL |

TABLE 1-continued

| Parameter | Nominal case | Worst case |
| --- | --- | --- |
| IPC capabilities | 0.008 mL | 0.012-0.014 mL |
| Filling process capabilities | 0.006 mL | 0.008 mL |

By adding these theoretical values to theoretical administered drug volumes of 1.15 mL and 1.10 mL, it was determined that in a nominal case the theoretical fill volume required to achieve an administered drug volume of 1.15 mL was 1.173 mL and the theoretical fill volume required to achieve an administered drug volume of 1.10 mL was 1.123 mL. In a worst case, the theoretical fill volume required to achieve an administered drug volume of 1.15 mL was determined to be 1.187 mL and the theoretical fill volume required to achieve an administered drug volume of 1.10 mL was determined to be 1.137 mL.

Next, these volumes were converted to "drug heights" within theoretical filled syringes using the dimensions of the syringes. The drug heights were then combined with the dimensions of the syringes and stopper assemblies to determine theoretical stopper positions in syringes filled with the desired theoretical fill volumes. "Stopper position" refers to the distance between the top of the stopper in a filled syringe and the distal side of the syringe flange (e.g. distance A in FIGS. 3A-3D of the present disclosure). A bubble height in each syringe was also taken into consideration. "Bubble height" refers to the distance between the fill line of the formulated drug substance in a filled syringe and the bottom of the stopper. It was first determined that, without overfilling, the stopper height would be 7.65+/−0.4 mm and the bubble height would be at 4 mm+/−1 mm. These values indicated that there would be no undesirable stopper compression, which could result in wrinkling, cracking, and/or failure to pass visual inspection, during insertion of the stopper into the syringe. Stopper heights for the desired overfill administered drug volumes (ADV) of 1.15 mL and 1.10 mL, assuming a fixed bubble height of 4.0 mm, were then calculated assuming nominal and worst case scenarios, and the above determined theoretical fill volumes, as follows:

TABLE 2

| Parameter | Origin | Nominal case 1.15 mL ADV (mm) | Worst case 1.15 mL ADV (mm) | Nominal case 1.10 mL ADV (mm) | Worst case 1.10 mL ADV (mm) |
| --- | --- | --- | --- | --- | --- |
| Body interior length | Drawing of syringe | 54.00 | 53.50 | 54.00 | 53.50 |
| Drug height | Calculated | 37.04 | 38.69 | 35.46 | 37.06 |
| Stopper height | Calculated | 7.85 | 8.25 | 7.85 | 8.25 |
| Body flange thickness | Drawing of syringe | 1.90 | 1.90 | 1.90 | 1.90 |
| Bubble height | Fixed | 4.00 | 4.00 | 4.00 | 4.00 |
| Stopper position | Calculated | 5.11 | 2.56 | 6.69 | 4.19 |

Next, it was determined that, in the filled and stoppered syringe being tested, the stopper was required to be a certain distance below the flange of the syringe in order to restrict the plunger rod of the stopper assembly from tilting far enough to deform the stopper, to an extent that could potentially compromise the integrity of the seal formed by the stopper. It was determined that the stopper would not deform to such an extent if the plunger rod was prevented from tilting at an angle of greater than 12° relative to a longitudinal axis of the syringe body. Based on provided dimensions of the syringe, stopper, and plunger, this length was determined to be 3.0 mm, with a tolerance of +/−0.5 mm. Thus, it was determined that at least a 2.5 mm distance, and more specifically a 3.0 mm+/−0.5 mm minimum distance, should be maintained between the top of the stopper in the filled syringe and the distal side of the syringe flange (e.g., distance A as illustrated in FIGS. 3A-3D).

Finally, it was determined that because the desired theoretical drug heights and stopper positions were not changeable in order to achieve an overfilled syringe without losing integrity of the stopper within the syringe body, the bubble height of 4.00 mm would theoretically be decreased. Using the worst case scenario drug heights and stopper positions, the bubble height for desired 1.15 mL ADV and 1.10 mL ADV were calculated as follows:

TABLE 3

| Parameter | Worst case 1.15 mL ADV (mm) | Worst case 1.10 mL ADV (mm) |
| --- | --- | --- |
| Body interior length | 53.50 | 53.50 |
| Drug fill volume | 1.173 mL | 1.123 mL |
| Drug height | 38.69 | 37.06 |
| Stopper height | 8.25 | 8.25 |
| Body flange thickness | 1.90 | 1.90 |
| Stopper position | 3.00 +/− 0.5 | 3.00 +/− 0.5 |
| Bubble height | 1.66 +/− 0.5 | 3.29 +/− 0.5 |

Example 2

A plurality of PFS were overfilled by machine as follows. Five formulated substances (87.7 mg/mL of an antibody A, 131.6 mg/mL antibody A, 175 mg/mL antibody A, a placebo solution, and water for injection (WFI)) were prepared and frozen at −80° C. Each formulated substance was removed from frozen storage and thawed for 16 hours. The formulated substances (except for WFI) were mixed, filtered, and transferred to an environment of 2-8° C. as follows:

TABLE 4

| Formulated Substance | Mixing Time | pH | Filtration Time | Filtration Yield | Total time of exposure at room temp. after thawing |
| --- | --- | --- | --- | --- | --- |
| Placebo | 15 min | 6.10 | 9 min | 96% | 30 min |
| 87.7 mg/mL antibody A | 12 min | 6.10 | 7 min | 94% | 50 min |
| 131.6 mg/mL antibody A | 11 min | 6.07 | 9 min | 91% | 71 min |
| 175 mg/mL antibody A | 11 min | 6.01 | 34 min | 81% | 106 min |

The redundant filtration lines consisted of two Millipak 20 units and ¼"×⅜" Pt cured silicone tubing for the product pathway. In the case of 175 mg/mL antibody A, two Millipak 20 units were initially used, and were switched out part of the way through with Millipak 40 units. A peristaltic pump was used as the motive force for filtration. All primary filters were tested and passed filter integrity as per standard EP-024.

The PFS filled in this procedure included 1 mL BD Hypak Physiolys SCF™ low tungsten syringes (Beckton Dickinson Medical), having a nominal volume of 1 mL. These syringes were paired with 1 mL BD Hypak PS Flurotec plunger stoppers and 1 mL BD Hypak 21510 PR C Plunger Rods (Beckton Dickinson Medical). The desired placement of the top of the stopper was at least 2.57 mm below the distal side of the syringe flange, and preferably between 5.0 mm and 2.56 mm below the distal side of the syringe flange. Alternatively, the desired placement of the rib of the stopper closest to the top of the stopper was at least 4.9 mm below the distal side of the syringe flange. Filling in this procedure was completed using an INOVA H3-5V commercial scale syringe filler. Stoppering was completed using a Becton Dickson Hypak stoppering unit. Stoppering height (e.g., distance between the top of the stopper and the distal side of the syringe flange) was measured using Vernier calipers.

The syringe filler was initially set up for a target fill volume of 1.28 mL. Using WFI, this resulted in an average deliverable volume of 1.27 mL for ten dispensed syringes. A vacuum stoppering tank setting of 70 mBar and 750 ms stoppering dwell time on the stoppering unit was initially used. At this fill volume and stoppering dwell time setting, stoppering was sometimes incomplete and WFI was drawn into the vacuum chamber.

The syringe filler was then set up for a target fill volume of 1.19 mL. This was targeted to maintain a minimum deliverable volume of 1.14 mL while providing a larger operating buffer for the vacuum stoppering setting and stopper placement requirement. The vacuum stoppering settings were kept between 70-75 mBar while the stopper dwell time was changed to 250 ms. When tested using WFI, this eliminated the problem of product suction into the vacuum chamber. The stoppering placement requirement (with the top of the stopper at least 3.0 mm below the distal side of the syringe flange) was, however, met on the stoppered syringes. A lower-than-desired stoppering consistency was achieved, but this was determined to be due to the clipped flanges of the syringes. To verify that the clipped flanges were the cause of the stoppering consistency, two tubs of 80 syringes each (160 syringes total) of round-flanged 1 mL-long syringes were used on the syringe filler. This resulted in a marked decrease in stoppering rejections, as compared to the stoppering rejections seen in the run with clipped-flange syringes.

The syringe filler set at a target fill volume of 1.19 mL was then used to fill syringes using WFI, the placebo, and the antibody A formulated substance. 160 syringes were filled with each of the five different fluids and at each of three different machine speeds (40%, 65%, and 90%) (with the exception of 87.7 mg/mL antibody A at 40% speed, for which only 35 syringes were filled, and 87.7 mg/mL antibody A at 65% speed, for which none were filled, due to an insufficient amount of product being available). All syringes were stoppered using a Hypak stoppering machine. Deliverable volumes from 20 filled and stoppered syringes from each batch were then measured. Deliverable volumes were measured by expelling volume from each of the 20 syringes, weighing the expelled volume, and converting the weight to volume using the following densities:

TABLE 5

| Formulated Substance | Density |
| --- | --- |
| Placebo | 1.023 g/mL |
| 87.7 mg/mL antibody A | 1.047 g/mL |
| 131.6 mg/mL antibody A | 1.059 g/mL |
| 175 mg/mL antibody A | 1.072 g/mL |

Deliverable volumes were calculated to be as follows:

TABLE 6

| Condition | Avg. Vol. (mL) | Max. Vol. (mL) | Min. Vol. (mL) |
|---|---|---|---|
| WFI - 40% speed | 1.18 | 1.19 | 1.16 |
| WFI - 65% speed | 1.17 | 1.18 | 1.17 |
| WFI - 90% speed | 1.18 | 1.20 | 1.15 |
| Placebo - 40% speed | 1.18 | 1.19 | 1.18 |
| Placebo - 65% speed | 1.18 | 1.19 | 1.18 |
| Placebo - 90% speed | 1.19 | 1.22 | 1.18 |
| 87.7 mg/mL antibody A - 40% speed | 1.17 | 1.19 | 1.15 |
| 87.7 mg/mL antibody A - 65% speed | N/A* | N/A* | N/A* |
| 87.7 mg/mL antibody A - 90% speed | 1.19 | 1.20 | 1.17 |
| 131.6 mg/mL antibody A - 40% speed | 1.16 | 1.19 | 1.14 |
| 131.6 mg/mL antibody A - 65% speed | 1.18 | 1.20 | 1.16 |
| 131.6 mg/mL antibody A - 90% speed | 1.17 | 1.19 | 1.15 |
| 175 mg/mL antibody A - 40% speed | 1.19 | 1.20 | 1.17 |
| 175 mg/mL antibody A - 65% speed | 1.18 | 211.1 | 1.17 |
| 175 mg/mL antibody A - 90% speed | 1.18 | 1.20 | 1.15 |

*Insufficient product was available to run this test.

Stoppering heights were measured from the top of the stopper to the distal side of the syringe flange, and were measured and calculated to be as follows:

TABLE 7

| Condition | Avg. Stoppering Height (mm) | Max. Stoppering Height (mm) | Min. Stoppering Height (mm) |
|---|---|---|---|
| WFI - 40% speed | 5.7 | 6.0 | 5.4 |
| WFI - 65% speed | 5.4 | 5.5 | 5.4 |
| WFI - 90% speed | 5.5 | 5.7 | 5.3 |
| Placebo - 40% speed | 5.4 | 5.5 | 5.4 |
| Placebo - 65% speed | 5.5 | 5.7 | 5.5 |
| Placebo - 90% speed | 5.8 | 6.0 | 5.5 |
| 87.7 mg/mL antibody A - 40% speed | 5.5 | 5.8 | 5.4 |
| 87.7 mg/mL antibody A - 65% speed | N/A* | N/A* | N/A* |
| 87.7 mg/mL antibody A - 90% speed | 5.5 | 6.0 | 5.4 |
| 131.6 mg/mL antibody A - 40% speed | 5.5 | 6.2 | 5.3 |
| 131.6 mg/mL antibody A - 65% speed | 5.5 | 5.6 | 5.4 |
| 131.6 mg/mL antibody A - 90% speed | 5.5 | 5.5 | 5.4 |
| 175 mg/mL antibody A - 40% speed | 5.4 | 5.5 | 5.2 |
| 175 mg/mL antibody A - 65% speed | 5.5 | 5.7 | 5.4 |
| 175 mg/mL antibody A - 90% speed | 5.5 | 6.0 | 5.4 |

*Insufficient product was available to run this test.

Example 3

A plurality of PFS were overfilled by hand as follows. Three formulated substances (87.7 mg/mL antibody A, 131.6 mg/mL antibody A, 175 mg/mL antibody A) were prepared and frozen at −80° C. Each substance was removed from frozen storage and thawed for 16 hours. The substances were mixed, filtered, and transferred to 2-8° C. as follows:

TABLE 8

| Formulated Substance | Mixing Time | pH | Filtration Time | Filtration Yield | Total time of exposure at room temp. after thawing |
|---|---|---|---|---|---|
| 87.7 mg/mL antibody A | 12 min | 6.04 | 7 min | 94% | 100 min |
| 131.6 mg/mL antibody A | 12 min | 6.11 | 11 min | 93% | 85 min |

TABLE 8-continued

| Formulated Substance | Mixing Time | pH | Filtration Time | Filtration Yield | Total time of exposure at room temp. after thawing |
|---|---|---|---|---|---|
| 175 mg/mL antibody A | 11 min | 6.02 | 21 min | 91% | 60 min |

The redundant filtration lines for 87.7 mg/mL antibody A and 131.6 mg/mL antibody A consisted of two Millipak 20s and ¼"×⅜" Pt cured silicone tubing for the product pathway. The redundant filtration lines for 175 mg/mL antibody A consisted of two Millipak 40s and ¼"×⅜" Pt cured silicone tubing for the product pathway. A peristaltic pump was used as the motive force for filtration.

The PFS filled in this procedure included 1 mL BD Hypak Physiolys SCF™ low tungsten syringes (Beckton Dickinson Medical), paired with 1 mL BD Hypak PS Flurotec plunger stoppers and 1 mL BD Hypak 21510 PR C Plunger Rods (Beckton Dickinson Medical). The desired placement of the top of the stopper was at least 3.0 mm below the distal side of the syringe flange. Filling in this procedure was completed by hand using a Watson-Marlow pump. Stoppering was completed using a Becton Dickson Hypak vacuum stoppering unit.

The target fill volume was set at 1.19 mL for this procedure. 160 syringes (in two tubs of 80 syringes each) were filled with each of the three different formulated substances. Deliverable volumes from 10 successfully filled and stoppered syringes from each batch were then measured. Deliverable volumes were measured by expelling volume from each syringe, weighing the expelled volume, and converting the weight to volume using the densities noted in Table 5. Deliverable volumes were calculated to be as follows:

TABLE 9

| Condition | Avg. Vol. (mL) | Max. Vol. (mL) | Min. Vol. (mL) |
|---|---|---|---|
| 87.7 mg/mL antibody A (Tub 1 of 2) | 1.19 | 1.23 | 1.15 |
| 87.7 mg/mL antibody A (Tub 2 of 2) | 1.18 | 1.22 | 1.17 |
| 131.6 mg/mL antibody A (Tub 1 of 2) | 1.18 | 1.21 | 1.16 |
| 131.6 mg/mL antibody A (Tub 2 of 2) | 1.18 | 1.18 | 1.15 |
| 175 mg/mL antibody A (Tub 1 of 2) | 1.17 | 1.20 | 1.15 |
| 175 mg/mL antibody A (Tub 2 of 2) | 1.16 | 1.17 | 1.15 |

As can be seen by comparing these volumes to those in Table 6, deliverable volumes of hand-filled syringes were comparable to deliverable volumes of machine-filled syringes.

Stoppering heights were measured for 15 hand-filled samples using Vernier calipers, and were taken, from the top of the stopper to the distal side of the syringe flange. Measurements were as follows:

TABLE 10

| Condition | Avg. Stoppering Height (mm) | Max. Stoppering Height (mm) | Min. Stoppering Height (mm) |
|---|---|---|---|
| 87.7 mg/mL antibody A (Tub 1 of 2) | 5.7 | 6.0 | 5.4 |
| 87.7 mg/mL antibody A (Tub 2 of 2) | 5.6 | 6.2 | 5.4 |
| 131.6 mg/mL antibody A (Tub 1 of 2) | 6.2 | 6.6 | 6.0 |
| 131.6 mg/mL antibody A (Tub 2 of 2) | 6.0 | 6.2 | 5.8 |

TABLE 10-continued

| Condition | Avg. Stoppering Height (mm) | Max. Stoppering Height (mm) | Min. Stoppering Height (mm) |
|---|---|---|---|
| 175 mg/mL antibody A (Tub 1 of 2) | 6.2 | 6.8 | 6.0 |
| 175 mg/mL antibody A (Tub 2 of 2) | 6.3 | 6.7 | 6.2 |

As can be seen by comparing these stoppering heights to those in Table 7, stoppering heights of hand-filled syringes were comparable to stoppering heights of machine-filled syringes.

The above description and examples are illustrative, and are not intended to be restrictive. One of ordinary skill in the art may make numerous modifications and/or changes without departing from the general scope of the invention. For example, and as has been described, the above-described embodiments (and/or aspects thereof) may be used in combination with each other. Additionally, portions of the above-described embodiments may be removed without departing from the scope of the invention. In addition, modifications may be made to adapt a particular situation or material to the teachings of the various embodiments without departing from their scope. Many other embodiments will also be apparent to those of skill in the art upon reviewing the above description.

The term "about" as used herein with respect to a value may refer to a variation of 10% above or below the stated value. Additionally, while a number of objects and advantages of the embodiments disclosed herein (and variations thereof) are described, not necessarily all such objects or advantages may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

What is claimed is:

1. A method of preparing a drug product, comprising:
    introducing a volume of a formulated drug substance into a primary packaging component, wherein the volume of the formulated drug substance is greater than a nominal volume of the primary packaging component; and
    positioning a stopper within the primary packaging component at a stopper position that is distal from a proximal end of the primary packaging component, wherein positioning the stopper comprises:
        determining the stopper position within the primary packaging component, wherein determining the stopper position includes determining a distance below a flange of the primary packaging component that restricts a plunger rod, connected to the stopper, from tilting to deform the stopper to an extent that compromises a seal formed by the stopper, and applying a vacuum to the stopper,
    wherein the primary packing component comprises a monolithic body, wherein the stopper is sized and configured to fit snugly within and adjacent to a wall of an interior of the body, and
    wherein the stopper position is at a position in which the plunger rod, connected to the stopper, is limited by the walls of the body to a maximum tilting angle of the plunger rod, with respect to a longitudinal axis of the body, and the maximum tilting angle of the plunger rod is an angle that is not sufficient to pull the stopper away from said wall of the body.

2. The method of claim 1, wherein the primary packaging component is a syringe.

3. The method of claim 1, wherein the primary packaging component is a prefillable syringe.

4. The method of claim 1, wherein the primary packaging component is a prefillable syringe having a nominal volume of at least 1 mL.

5. The method of claim 1, wherein the volume of the formulated drug substance is at least 0.05 mL greater than the nominal volume of the primary packaging component.

6. The method of claim 1, wherein the formulated drug substance comprises one of a protein, a nucleic acid, or a gene therapy medicament.

7. The method of claim 1, wherein the formulated drug substance comprises an antibody and at least one excipient.

8. The method of claim 1, wherein the formulated drug substance comprises an antibody solution, wherein antibody is present in the solution at a concentration of at least 100 mg/mL.

9. The method of claim 1, wherein the formulated drug substance comprises an antibody and has a viscosity of at least 5 cPoise.

10. A method of preparing a plurality of drug products, the method comprising repeating the steps of claim 1 for each of a plurality of primary packaging components in a batch.

11. The method of claim 10, wherein the batch of primary packaging components comprises 80 prefilled syringes.

12. The method of claim 1, wherein the primary packaging component is a prefillable syringe, the nominal volume is 1 mL, and the stopper position is such that an end of the stopper closest to a flange of the syringe is between about 2.5 mm and about 5.0 mm away from the flange of the syringe.

13. The method of claim 1, wherein the volume of the formulated drug substance is between 1.05 mL and 1.30 mL.

14. The method of claim 1, wherein the volume of the formulated drug substance is between about 110% and about 140% of the nominal volume of the primary packaging component.

15. The method of claim 1, wherein applying the vacuum to the stopper of the primary packaging component includes subjecting the stopper of the primary packaging component to a pressure of between 70 and 75 m Bar.

16. The method of claim 1, wherein the maximum tilting angle of the plunger rod is 20°.

17. The method of claim 16, wherein the nominal volume of the primary packaging component is 1 mL.

18. A method of preparing a drug product, comprising:
    determining a theoretical fill volume, wherein the theoretical fill volume is a sum of a theoretical lost volume and a theoretical administered drug volume;
    determining a drug height based on the theoretical fill volume and dimensions of a prefillable syringe;
    introducing a volume of a formulated drug substance into the prefillable syringe comprising a body, wherein the volume of the formulated drug substance corresponds to the theoretical fill volume and is between about 110% and 140% of a nominal volume of the prefillable syringe; and
    positioning a stopper within the prefillable syringe at a stopper position that is distal from a proximal end of the prefillable syringe, thereby sealing the introduced volume of the formulated drug substance,
    wherein positioning the stopper comprises:
        determining a stopper position within the prefillable syringe, wherein determining the stopper position includes determining a distance below a flange of the prefillable syringe that restricts a plunger rod, connected to the stopper, from tilting to deform the stopper to an extent that comprises a seal formed by the stopper, and applying a vacuum to the stopper, wherein the stopper is sized and configured to fit snugly within a wall of an interior of the body, wherein, at the stopper position, the plunger rod, connected to the stopper, is limited by the walls of the body to a maximum tilting angle, with respect to a longitudinal axis of the body, and the maximum tilting angle of the plunger rod is an angle that is not sufficient to pull the stopper away from said wall of the body.

19. The method of claim 18, wherein the nominal volume of the syringe is 1 mL.

20. The method of claim 18, wherein the stopper position is such that an end of the stopper closest to a flange of the prefillable syringe is between about 1 mm and about 5.5 mm away from the flange of the prefillable syringe.

21. The method of claim 18, further comprising:

determining the stopper position based on the determined drug height and the dimensions of the prefillable syringe.

22. A method of preparing a drug product, comprising:

determining a theoretical fill volume, wherein the theoretical fill volume is a sum of a theoretical lost volume and a theoretical administered drug volume;

determining a drug height based on the theoretical fill volume and dimensions of a prefillable syringe;

introducing a volume of a formulated drug substance into the prefillable syringe comprising a body, wherein the volume of the formulated drug substance corresponds to the theoretical fill volume and is greater than a nominal volume of the prefillable syringe;

determining a stopper position within the prefillable syringe based on the drug height and the dimensions of the prefillable syringe, wherein the stopper position is distal from a proximal end of the prefillable syringe; and positioning a stopper within the prefillable syringe at the stopper position by applying a vacuum to the stopper, thereby sealing the introduced volume of the formulated drug substance, wherein the stopper is sized and configured to fit snugly within a wall of an interior of the body, and wherein determining the stopper position includes determining a distance below a flange of the prefillable syringe that restricts a plunger rod, connected to the stopper, from tilting to deform the stopper to an extent that compromises the seal formed by the stopper.

* * * * *